(12) United States Patent
Gerbec et al.

(10) Patent No.: US 6,562,074 B2
(45) Date of Patent: May 13, 2003

(54) ADJUSTABLE BONE FUSION IMPLANT AND METHOD

(75) Inventors: Daniel E. Gerbec, Logan, UT (US); T. Wade Fallin, Hyde Part, UT (US); Tom Faciszewski, Marshfield, WI (US)

(73) Assignee: MedicineLodge, Inc., Logan, UT (US)

( * ) Notice: Subject to any disclaimer, the term of this patent is extended or adjusted under 35 U.S.C. 154(b) by 0 days.

(21) Appl. No.: 10/121,630

(22) Filed: Apr. 12, 2002

(65) Prior Publication Data

US 2003/0074064 A1 Apr. 17, 2003

Related U.S. Application Data

(63) Continuation-in-part of application No. 09/981,674, filed on Oct. 17, 2001.

(51) Int. Cl.[7] .................................................. A61F 2/28
(52) U.S. Cl. .................................................... 623/17.15
(58) Field of Search ............................ 623/16.11, 17.11, 623/17.15, 17.16; 606/60, 61, 62, 63

(56) References Cited

U.S. PATENT DOCUMENTS

| | | | |
|---|---|---|---|
| 4,657,550 A | 4/1987 | Daher | |
| 4,834,757 A | 5/1989 | Brantigan | |
| 4,863,476 A | 9/1989 | Shepperd | |
| 5,059,193 A | 10/1991 | Kuslich | |
| 5,171,278 A | 12/1992 | Pisharodi | |
| 5,290,312 A | 3/1994 | Kojimoto et al. | |
| 5,306,310 A | 4/1994 | Siebels | |
| 5,336,223 A | 8/1994 | Rogers | |
| 5,390,683 A | 2/1995 | Pisharodi | |
| 5,405,391 A | 4/1995 | Hednerson et al. | |
| 5,425,772 A | 6/1995 | Brantigan | |
| 5,443,514 A | 8/1995 | Steffee | |
| 5,458,641 A | 10/1995 | Ramirez Jimenez | |
| 5,554,191 A | 9/1996 | Lahille et al. | |
| 5,571,192 A | 11/1996 | Schonhoffer | |
| 5,653,762 A | 8/1997 | Pisharodi | |
| 5,653,763 A | 8/1997 | Errico et al. | |
| 5,658,335 A | 8/1997 | Allen | |
| 5,665,122 A | * 9/1997 | Kambin | 623/17.16 |
| 5,693,100 A | 12/1997 | Pisharodi | |
| 5,702,455 A | 12/1997 | Saggar | |
| 5,716,415 A | 2/1998 | Steffee | |
| 5,776,198 A | 7/1998 | Rabbe et al. | |
| 5,782,832 A | 7/1998 | Larsen et al. | |
| 5,865,848 A | 2/1999 | Baker | |
| 5,980,522 A | * 11/1999 | Koros et al. | 606/61 |
| 5,989,290 A | 11/1999 | Biedermann et al. | |
| 6,015,436 A | 1/2000 | Schonhoffer | |
| 6,045,579 A | 4/2000 | Hochshuler et al. | |
| 6,080,193 A | 6/2000 | Hochshuler et al. | |
| 6,093,207 A | 7/2000 | Pisharodi | |

(List continued on next page.)

Primary Examiner—Eduardo C. Robert
Assistant Examiner—David A Bonderer
(74) Attorney, Agent, or Firm—Workman, Nydegger & Seeley

(57) ABSTRACT

An adjustable bone fusion implant includes a first plate having an interior face with a plurality of spaced apart first support members projecting therefrom. Each support member has a plurality of teeth projecting therefrom. A second plate has an interior face with a plurality of spaced apart second support members projecting therefrom. Each second support member has at least one tooth or one adjustment hole formed thereon. A portion of the plurality of teeth of each first support member mechanically engage with the at least one tooth or one adjustment hole of a corresponding second support member so that the first plate and the second plate can be selectively separated forming a compartment therebetween. A reinforcing member is disposed between the first plate and the second plate such that the application of a compressive force between the first plate and the second plate applies compression on the reinforcing member.

37 Claims, 27 Drawing Sheets

U.S. PATENT DOCUMENTS

| | | | |
|---|---|---|---|
| 6,102,950 A | * | 8/2000 | Vaccaro .................. 623/17.16 |
| 6,117,174 A | | 9/2000 | Nolan |
| 6,126,689 A | | 10/2000 | Brett |
| 6,129,763 A | * | 10/2000 | Chauvin et al. ......... 623/17.11 |
| 6,159,244 A | * | 12/2000 | Suddaby .................. 623/17.11 |
| 6,174,334 B1 | | 1/2001 | Suddaby |
| 6,176,881 B1 | | 1/2001 | Schar et al. |
| 6,183,517 B1 | | 2/2001 | Suddaby |
| 6,190,413 B1 | | 2/2001 | Sutcliffe |
| 6,190,414 B1 | | 2/2001 | Young et al. |
| 6,193,755 B1 | | 2/2001 | Metz-Stavenhagen et al. |
| 6,193,756 B1 | | 2/2001 | Studer et al. |
| 6,193,757 B1 | * | 2/2001 | Foley et al. ............. 623/17.16 |
| 6,200,348 B1 | | 3/2001 | Biedermann et al. |
| 6,296,647 B1 | * | 10/2001 | Robioneck et al. ......... 606/105 |
| 6,299,644 B1 | * | 10/2001 | Vanderschot ............. 623/17.15 |
| 6,332,895 B1 | | 12/2001 | Suddaby |
| 6,395,034 B1 | * | 5/2002 | Suddaby .................. 623/17.15 |
| 6,419,705 B1 | | 7/2002 | Erickson |
| 2001/0032017 A1 | | 10/2001 | Alfaro et al. |
| 2002/0010511 A1 | | 1/2002 | Michaelson |

* cited by examiner

ADJUSTABLE BONE FUSION IMPLANT AND METHOD

CROSS-REFERENCE TO RELATED APPLICATIONS

This application is a continuation-in-part of U.S. patent application Ser. No. 09/981,674, filed Oct. 17, 2001.

BACKGROUND OF THE INVENTION

1. The Field of the Invention

The present invention relates generally to surgical devices and methods for fusing adjacent bone structures and, more specifically, to surgical devices and methods for fusing adjacent vertebrae.

2. The Relevant Technology

The spinal column is made up of thirty-three vertebra each separated by a cushioning disc. Disease and trauma can damage these discs, creating instability that leads to loss of function and excruciating pain. Spinal fusion implants provide a successful surgical outcome by replacing the damaged disc and restoring the spacing between the vertebra, eliminating the instability and removing the pressure on neurological elements that cause pain. The fusion is accomplished by providing an implant which recreates the natural intervertebral spacing and which has an internal cavity with outwardly extending openings. The internal cavity is commonly filled with osteogenic substances, such as autogenous bone graft or bone allograft, to cause the rapid growth of a bony column through the openings of the implant.

Recently, adjustable fusion implants have been developed that allow the surgeon to adjust the height of the implant. This provides an ability to intra-operatively tailor the implant height to match the natural spacing between the vertebrae. This reduces the number of sizes that the hospital must keep on hand to match the variable anatomy of the patients. However, the prior art is replete with adjustable fusion implants that have an active mechanism for expanding the implant to change its height. Active mechanism refers to a mechanical structure built into the implant to cause the change in the height dimension. The presence of the active mechanism significantly decreases the amount of internal space available for placement of bone graft and other osteogenic substances to encourage the bony fusion between the adjacent vertebrae. It would therefore be an improvement over the prior art to provide an adjustable fusion implant that does not require the presence of an active mechanism, thereby maximizing the internal space for osteogenic substances and providing a better inducement for bony fusion.

Other adjustable fusion implants known in the art are comprised of modular components that must be pre-assembled prior to implantation. It would therefore be an advantage to provide a fusion implant that can be adjusted in situ.

Another challenge associated with spinal fusion is the restoration of the curvature of the spine. This curvature is present at each intervertebral level at varying degrees, and is manifested by a different spacing or height at the anterior and posterior margins of adjacent vertebral bodies. For example, the lumbar spine has a natural curvature when viewed from a lateral perspective referred to as lordosis, where the mid section of the lumbar spine is more anterior than the end sections. Thus, at any given intervertebral level, the intervertebral height at the posterior margin is less than the intervertebral height at the anterior margin, resulting in a wedge shaped disc or intervertebral space.

When a spinal fusion implant is placed from the posterior aspect of the vertebra, it must be sized to fit through the smaller posterior space, resulting in an undersized fit at the anterior end once the implant is in place. When the vertebral bodies are made to contact the opposing surfaces of the fusion implant, the curvature of the spine is straightened, producing higher stresses in adjacent levels of the spinal column and potentially leading to faster degeneration of adjacent intervertebral discs. Because some clinical problems require surgery from the posterior approach, it would be desirable to install an intervertebral fusion implant from the posterior side of the patient. It would therefore be an improvement to provide a spinal fusion implant that could recreate the natural curvature of the spine by reproducing the wedge shaped intervertebral space and concurrently allow for installation from the narrow side of the intervertebral space.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
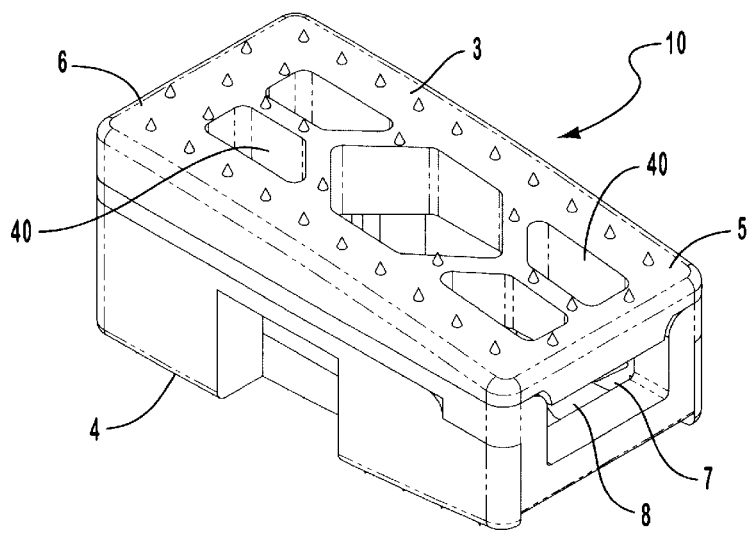
FIG. 1 is a perspective view of one embodiment of an adjustable bone fusion implant in an assembled state.

Depicted in FIG. 1 is one embodiment of an inventive adjustable bone fusion implant 10 incorporating features of the present invention. Fusion implant 10 is designed for placement between bones and/or pieces of bone to facilitate fusing of the bone matter together. Considered as a whole, in the embodiment depicted fusion implant 10 has a substantially rectangular box shaped configuration with a top surface 3 and an opposing bottom surface 4 that extend between a proximal end 5 and an opposing distal end 6. Fusion implant 10 has an interior surface 7 that bounds a compartment 8. A plurality of grafting ports 40 extend through fusion implant 10 so as to communicate with compartment 8. Either before, during, and/or after positioning of fusion implant 10 between bone matter, compartment 8 is at least partially packed with an osteogenic substance. As used in the specification and appended claims, the term "osteogenic substance" is broadly intended to include natural bone, such as autogenous bone graft or bone allograft, synthetic bone, growth factors and cytokines (including bone morphogenic proteins), and/or combinations thereof. Once fusion implant 10 is disposed between the bone matter, the osteogenic substance causes the rapid growth of a bony column through grafting ports 40, thereby forming the bone matter into a solid continuous bone.

In the embodiment depicted, fusion implant 10 has a substantially wedged shaped configuration. That is, the height of fusion implant 10 at proximal end 5 is shorter than the height at distal end 6. The wedged shaped configuration facilitates placement of fusion implant 10 in wedged shaped openings such as between select vertebrae for fusing the vertebrae together. In alternative embodiments, it is appreciated that fusion implant 10 can be configured at any desired wedge angle or can have substantially parallel top and bottom surfaces. Furthermore, fusion implant 10 need not have a rectangular box shaped configuration but can be square, circular, or have any other polygonal or irregular configuration.

Figure 2:
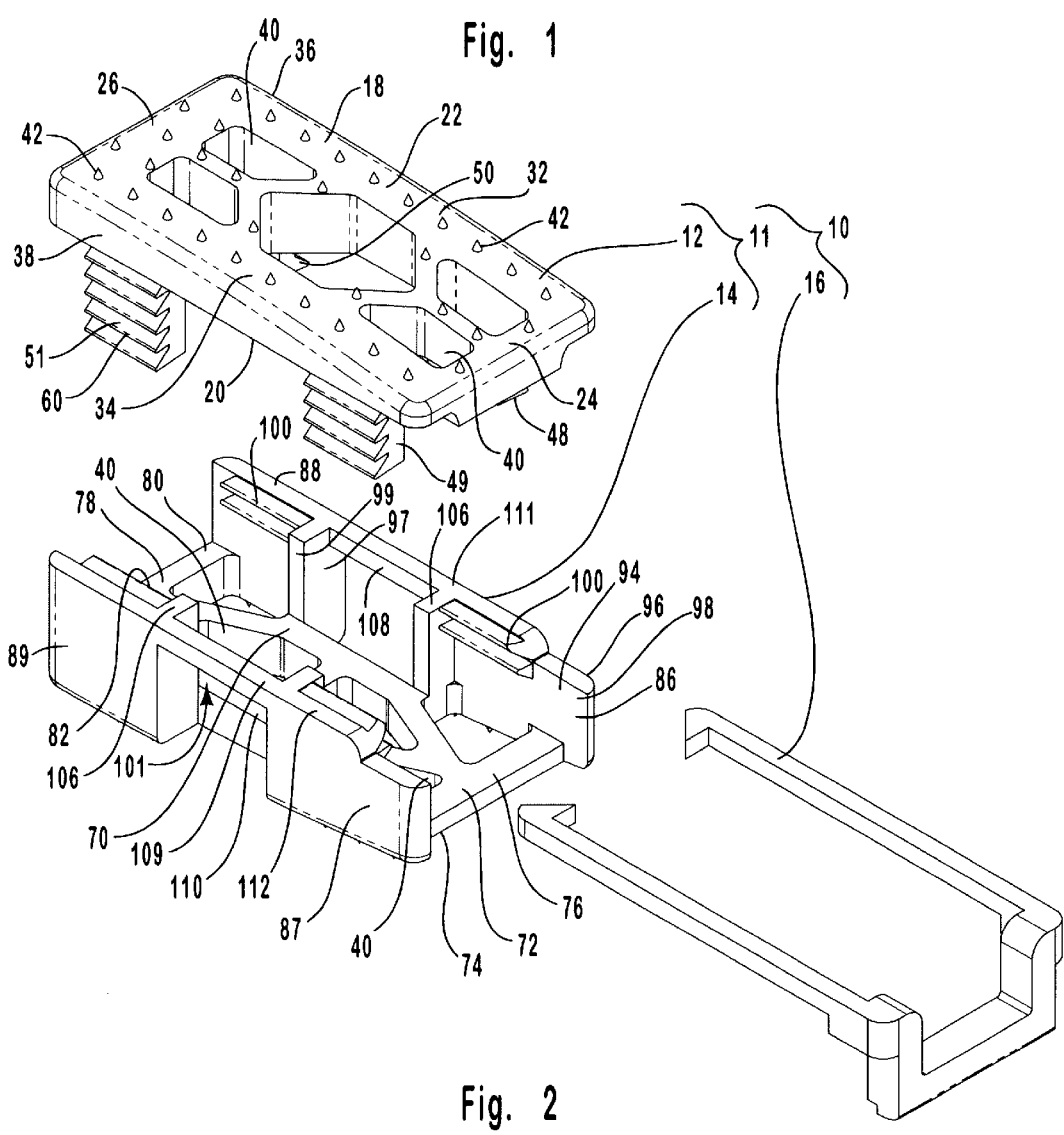
FIG. 2 is a perspective view of the embodiment shown in FIG. 1 in a disassembled state.

As depicted in FIG. 2, fusion implant 10 comprises a housing 11 and a reinforcing member 16. Housing 11 comprises a cap 12 that is selectively connected to a base 14. Cap 12 comprises a cap plate 18 having an interior face 20 and an opposing exterior face 22 that each extend between a proximal end 24 and an opposing distal end 26. The term "plate" as used in the specification and appended claims is broadly intended to include not only structures that have a flat or substantially flat surface but also, for example, members that are curved, sloped, have regular or irregular formations thereon, and that may or may not have openings extending therethrough.

Figure 3A:
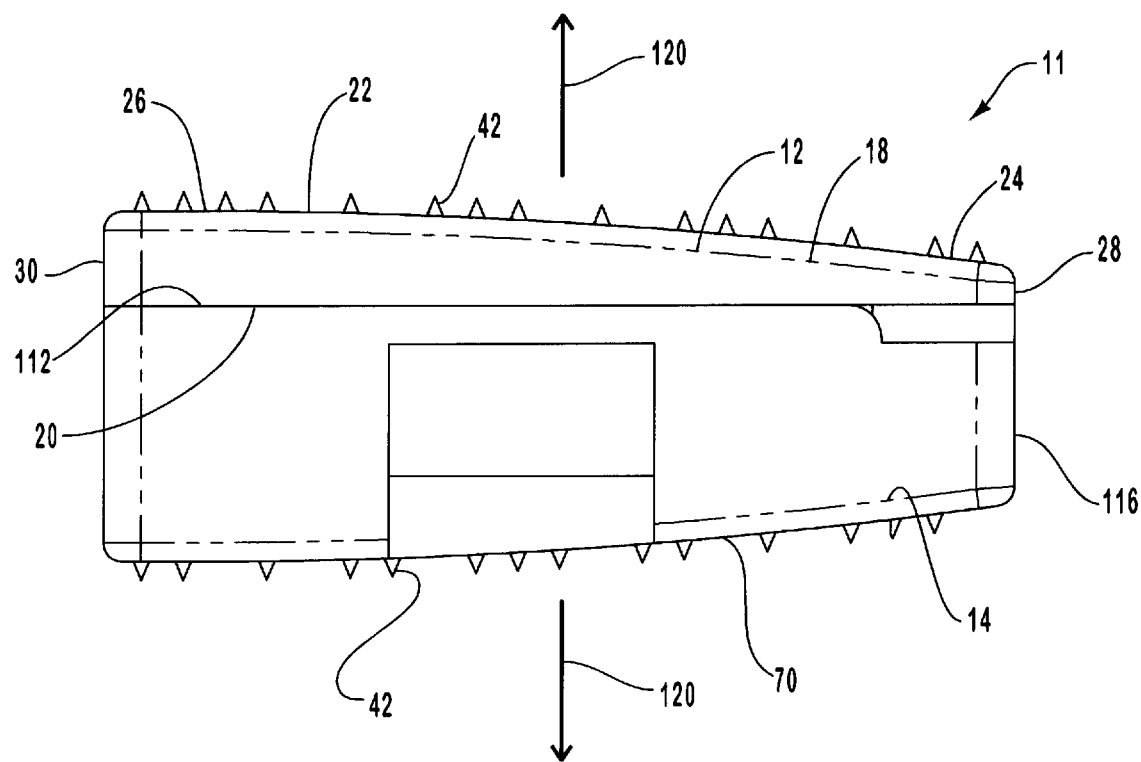
FIG. 3A is an elevated side view of the housing of the embodiment shown in FIG. 1 in a fully collapsed state.
Figure 3B:
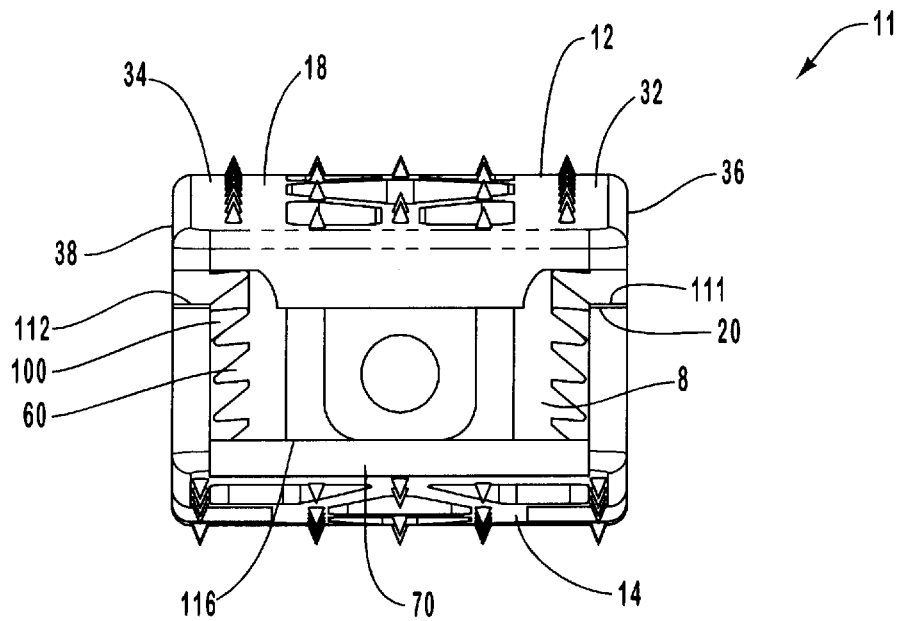
FIG. 3B is an elevated front end view of the embodiment shown in FIG. 3A.

As shown in FIG. 3A, proximal end 24 of cap plate 18 terminates at an end face 28 while distal end 26 terminates at a distal end face 30. Exterior face 22 is sloped relative to interior face 20 such that cap plate 18 has a wedged shaped configuration with end face 28 being shorter than end face 30. In alternative embodiments, either or both of faces 20 and 22 can be sloped or both horizontally disposed in parallel alignment. As depicted in FIGS. 2 and 3B, faces 20 and 22 also extend between opposing sides 32 and 34. Sides 32 and 34 terminate at side faces 36 and 38, respectively.

Extending through cap plate 18 from exterior face 22 to interior face 20 are a plurality of grafting ports 40. In one embodiment grafting ports 40 comprise about 25 percent to about 50 percent and more commonly about 25 percent to about 35 percent of the surface area of exterior face 22 of cap plate 18 that contacts bone. In alternative embodiments, it is appreciated that any number of grafting ports 40 can be used and that each grafting port can have any desired configuration or size. It is also appreciated that cap plate 18 can be formed with no grafting ports 40 extending therethrough.

Upwardly projecting from exterior face 22 of cap plate 18 are a plurality of retention barbs 42. Retention barbs 42 function to frictionally engage with adjacent bone so as to enhance fixation and resist implant migration or movement of fusion implant 10 relative to the bone. In alternative embodiments, it is appreciated that any number of one or more retention barbs 42 can be mounted on cap plate 18 and that barbs 42 can have any desired configuration so as to effectively engage with bone. For example, in alternative embodiments barbs 42 can comprise discrete teeth or aligned racks of teeth. It is also appreciated that barbs can be oriented at a common or at different angles so as to more effectively prevent movement in a specific direction.

Figure 4A:
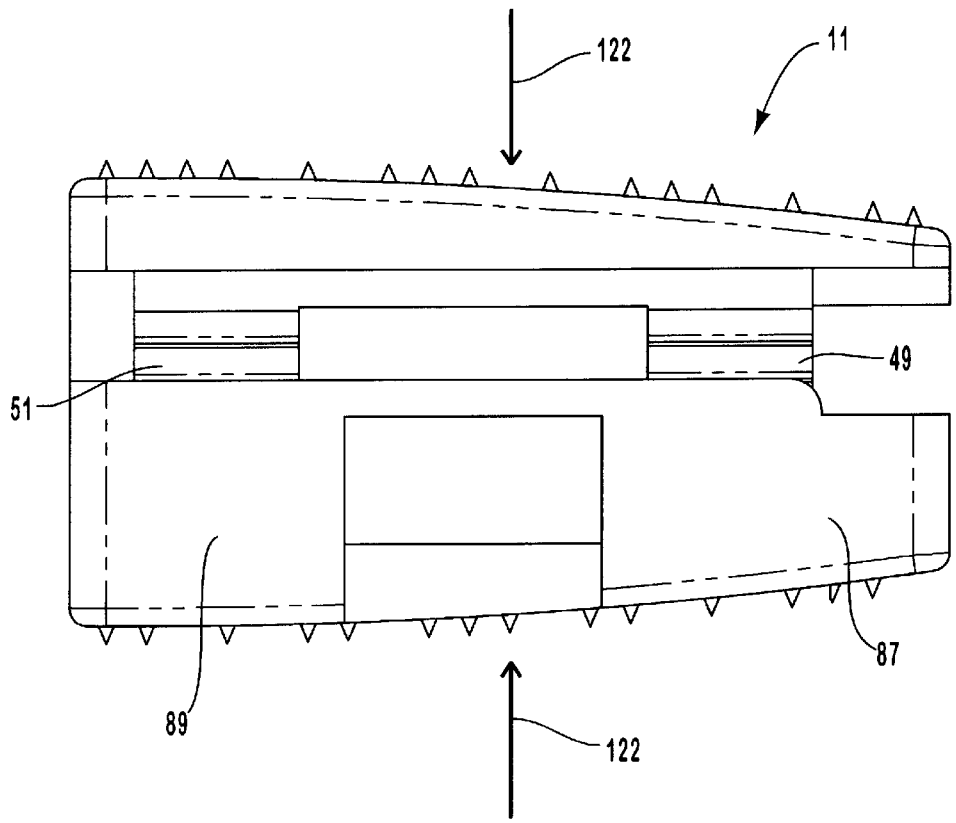
FIG. 4A is an elevated side view of the embodiment shown in FIG. 3A in a partially expanded state.
Figure 4B:
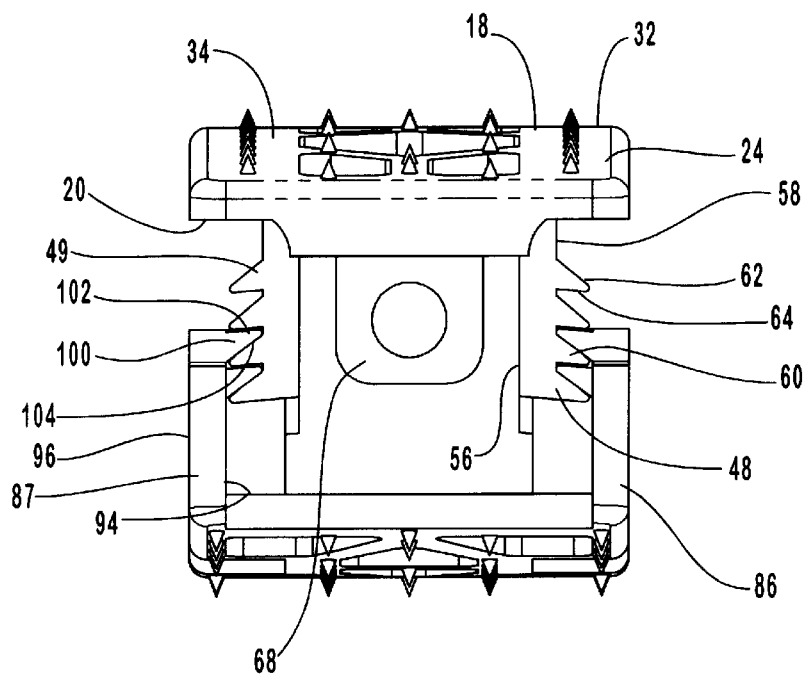
FIG. 4B is an elevated front end view of the embodiment shown in FIG. 4A.

As perhaps best depicted in FIGS. 2, 4A, and 4B, a plurality of support members downwardly project from interior face 20 of cap plate 18. More specifically, a first pair of spaced apart support members 48 and 49 downwardly project along sides 32 and 34 of cap plate 18 at proximal end 24. Similarly, a pair of spaced apart support members 50 and 51 downwardly project along sides 32 and 34 of cap plate 18 at distal end 26. As shown in FIG. 4B each support member has an inside face 56 and an outside face 58. Outwardly projecting on outside face 58 is a rack or plurality of teeth 60. Each tooth 60 has a downwardly sloping top surface 62 and a substantially horizontally disposed bottom surface 64. In an alternative embodiment, bottom surface 64 can also be downwardly sloping. In one embodiment, teeth 60 have a spacing in a range between about 0.5 mm to about 2 mm and more commonly in a range between about 0.5 mm to about 1 mm. In alternative embodiments, teeth 60 can be spaced at any desired increments.

Figure 4C:
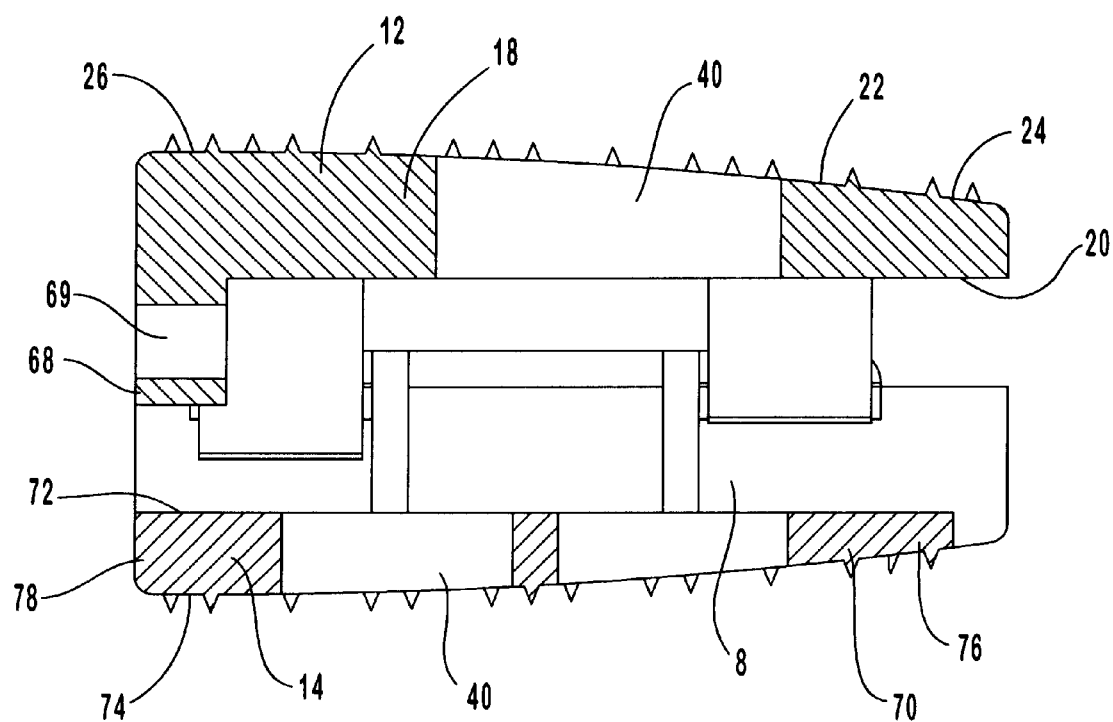
FIG. 4C is a cross sectional side view of the embodiment shown in FIG. 4A.

As depicted in FIGS. 4B and 4C, an attachment wall 68 downwardly projects from interior face 20 of cap plate 18 at distal end 26. In one embodiment of the present invention, means are provided for removably connecting an insertion tool to attachment wall 68. By way of example and not by limitation, a threaded aperture 69 extends through attachment wall 68. In this configuration, threaded aperture 69 communicates with compartment 8 within fusion implant 10. As will be discussed below, threaded aperture 69 enables threaded coupling with an insertion tool. In alternative embodiments for the means, threaded aperture 69 need not extend all the way through attachment wall 68. Furthermore, threaded aperture 69 can be replaced with a hole or recess having bayonet prongs projecting therefrom for engaging a bayonet connector. Such prongs can also project from attachment wall 68. In yet other embodiments, a head, socket, or other conventional connector can be formed on attachment wall 68.

Returning to FIG. 2, base 14 includes a base plate 70 that is comparable to cap plate 18. That is, base plate 70 also includes an interior face 72 and an exterior face 74 that each extend between a proximal end 76 and an opposing distal end 78. Faces 72 and 74 likewise extend between opposing sides 80 and 82. Extending through base plate 70 between interior face 72 and exterior face 74 are a plurality of grafting ports 40. The grafting ports in base plate 70 can be positioned in the same alternative number, size, and configuration as discussed above with regard to grafting ports 40 on cap plate 18. Outwardly projecting from exterior face 74 are a plurality of retention barbs 42. Retention barbs 42 on base plate 70 can also have the same alternative size, configuration, and orientation as retention barbs 42 on cap plate 18.

As depicted in FIG. 4C, exterior face 74 of base plate 70 is sloped relative to interior face 72 so that base plate 70 is thicker at distal end 78 than at proximal end 76. As with cap plate 18, base plate 70 can also have a constant thickness with both faces 72 and 74 being either sloped or horizontally disposed. Furthermore, each of faces 72 and 74 can be sloped at different angles. Although not required, in the embodiment depicted interior face 72 of base plate 70 is disposed substantially parallel to interior face 20 of cap plate 18. As previously discussed, in alternative embodiments it is appreciated that only one of exterior faces 22 and 74 can be sloped or, if desired, neither face can be sloped.

Returning to FIG. 2, a plurality of support members also upwardly extend from base plate 70. Specifically, a pair of spaced apart support members 86 and 87 upwardly extend from sides 80 and 82, respectively, of base plate 70 at proximal end 76. Similarly, a pair of spaced apart support members 88 and 89 upwardly project from sides 80 and 82, respectively, of base plate 70 at distal end 78. As depicted in FIG. 2, each support member 86–89 of base plate 70 has an inside face 94 and an opposing outside face 96 that each extend to a free top end 98. Extending between support members 86 and 88 at top end 98 is a brace 108. Brace 108 and support members 86 and 88 form an exposed biasing rail 111 that runs the length of side 80 of base plate 70. A brace 109 extends between support members 87 and 89 at top ends 98 thereof. Brace 109 and support members 87 and 89 form an exposed biasing rail 112 that runs the length of side 82 of base plate 70. Formed below each brace 108 and 109 is a side port 110 that communicates with compartment 8. In part, each side port 110 acts as a grafting port to facilitate bone growth.

Inwardly projecting from inside face 94 at top end 98 of each support member 86–89 are a pair of adjacently disposed teeth 100. As seen in FIG. 4B, each tooth 100 has a horizontally disposed top surface 102 and an upwardly slopping bottom surface 104. Returning to FIG. 2, a retention wall 106 inwardly projects from each support member 86–89 between teeth 100 and side ports 110. As discussed later in greater detail, each retention wall 106 functions as a stop.

Each retention wall 106 has an inside face 97 that extends to an end face 99. Each inside face 97 faces one of side ports 110. It is noted that at each side port 110, base plate 70 extends only to end face 99 of each retention wall 106. Furthermore, braces 108 and 109 only extend part way toward end face 99 of retention walls 106. As such, there is an open vertical channel 101 formed between each pair of adjacent retention walls 106. Each vertical channel 101 extends along the height of inside face 97 of retention walls 106 adjacent to where each inside face 97 intersects with end face 99. As such, the top of each vertical channel 101 is located inside of braces 108 and 109. As discussed later in greater detail, vertical channels 101 can be used for the initial attachment of cap 12 to base 14.

The above described cap 12 and base 14 are configured for mechanical mating. Specifically, as depicted in FIGS. 3A and 3B, cap 12 is configured to mate with base 14 such that interior face 20 of cap plate 18 can selectively rest on biasing rails 111 and 112 of base 14. In this configuration, teeth 60 on support members 49–51 of cap 12 complementary mesh with teeth 100 on corresponding support members 86–89 of base 14. In this assembled configuration, compartment 8 is formed between cap plate 18 and base plate 70. An access mouth 116 is formed at the proximal end of assembled housing 11 and provides access to compartment 8.

As a separation force is applied to cap 12 and base 14 in the directions indicated by arrows 120 in FIG. 3A, the complementary upwardly sloping surfaces 62 and 104 on teeth 60 and 100 create an inward flexing movement of support members 48–51 on cap 12 and/or an outward flexing movement of support members 86–89 on base 14. This flexing of the support members enables the teeth to ride over each other. As a result, as depicted in FIGS. 4A and 4B, housing 11 can be selectively expanded by predefined incremental amounts into predefined positions. The incremental amounts are based on the spacing of the teeth.

In contrast, as a compression force is applied to cap 12 and base 14 in the directions indicated by arrows 122 depicted in FIG. 4A, the mating horizontal surfaces 64 and 102 of teeth 60 and 100 press against one another so as to provide a mechanical stop that precludes the collapse of housing 11. Any compression of housing 11 is due either to elastic compression of the material or failure of housing 11. It is appreciated that retention walls 106 preclude horizontal sliding between cap 12 and base 14 when they are secured together. That is, support members 48–51 and/or teeth 60 thereon of cap 12 bias against retention walls 106, which act as a stop when any transverse force is applied so as to attempt to horizontally separate cap 12 and base 14.

In one embodiment of the present invention, means are provided for connecting cap plate 18 to base plate 70 such that cap plate 18 and base plate 70 can be selectively manually separated to one or more predefined positions and such that cap plate 18 and base plate 70 are mechanically stopped from collapsing toward each other once separated to the one or more predefined positions. By way of example and not by limitation, one embodiment of such means comprises support members 48–51 and 86–89 with interacting teeth 60 and 100 as described above. The support members also combine together to form expandable sidewalls.

In alternative embodiments, it is appreciated that the orientation of the various support members and their corresponding teeth can be reversed between cap 12 and base 14. It is also appreciated, that each of teeth 60 and 100 can each be formed in various combinations of one or more teeth. Furthermore, rather than having four support members on each of cap plate 18 and base plate 70, it is appreciated that a single elongated support member can be centrally disposed on each side of cap plate 18 and base plate 70. In this embodiment, a retention wall is mounted on each opposing end of each support member on one plate so as to prevent sliding movement therebetween.

In an alternative embodiment, for reasons as will become apparent below, it is also envisioned that teeth 60 and 100 can be formed with an opposing sloping face on each side such that cap plate 18 and base plate 70 can be selectively separated by the application of the separation force and selectively collapsed by the application of the compression force 122. Furthermore, teeth 60 and 100 can have a variety of other conventional configurations which would enable the teeth to mesh together and still enable selective separation of cap plate 18 and base plate 70.

In one embodiment housing 11 depicted in FIGS. 4A and 4B can withstand a compression force 122 of over 400 pounds without failure or producing permanent deformation. As such, depending on the intended use, housing 11 can independently comprise fusion implant 10. In other situations, however, it is desirable that housing 11 be able to withstand a significantly greater compressive force 122 prior to failure or permanent deformation. In such situations, reinforcing member 16 is used.

Figure 5A:
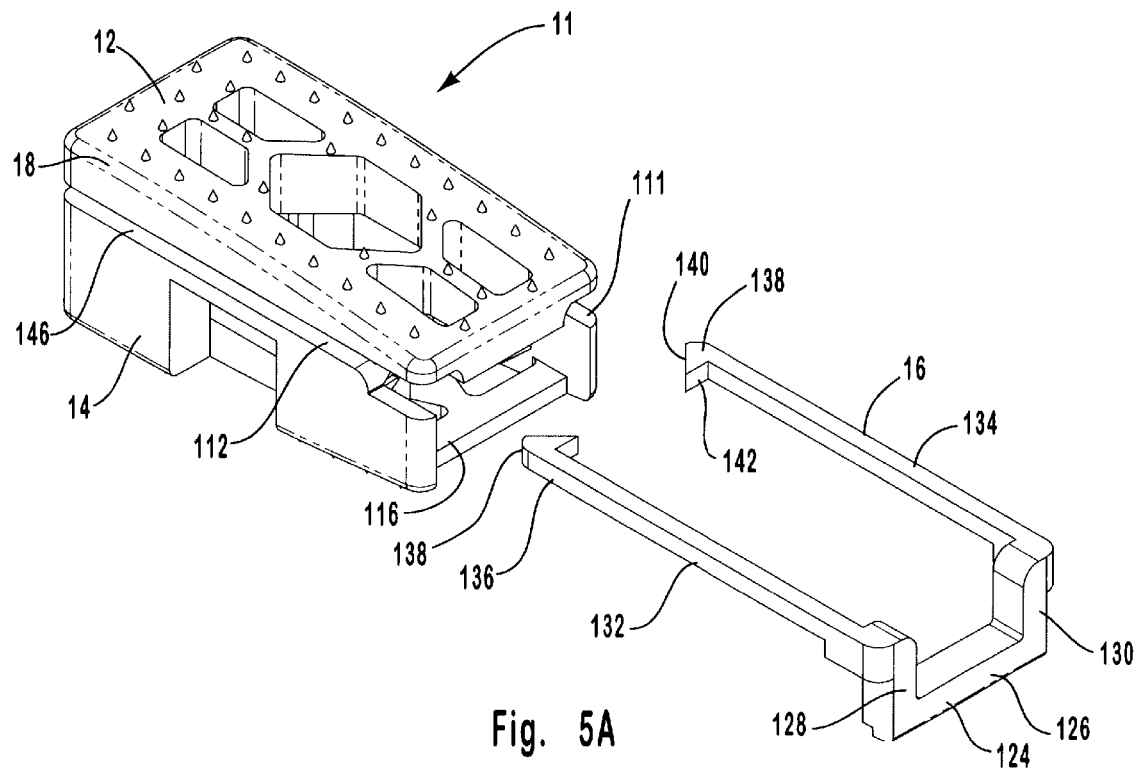
FIG. 5A is a perspective view of the partially expanded fusion implant shown in FIG. 4A configured to receive a reinforcing member.

As depicted in FIG. 5A, reinforcing member 16 is in the form of a substantially U-shaped clip. Specifically, reinforcing member 16 comprises a substantially U-shaped cantilever beam 124 which includes an elongated base 126 having supports 128 and 130 upstanding from each opposing end thereof. Forwardly projecting from the top end of support 128 and 130 is an elongated flexible arm 132 and 134, respectively. Each arm 132 and 134 terminates at a free end 136 having an inwardly facing latching barb 138 formed thereat. Each latching barb 138 has a sloped forward surface 140 and an orthogonally disposed inside surface 142. Reinforcing member 16 has a width extending between the outside of opposing arms 132 and 134 that is substantially the same as the maximum width of cap 12 and base 14.

Once cap 12 is selectively elevated relative to base 14, a gap 146 is formed between cap plate 18 and each biasing rail 111 and 112. Reinforcing member 16 is configured such that each arm 132 and 134 can be slidably received within a corresponding gap 146 on each side of housing 11. Sloping surface 140 on each latching barb 138 biases against support members 48–51 and/or the threads thereon causing arms 132, 134 and/or cantilever beam 124 to outwardly bend, thereby enabling latching barbs 138 to pass over support members 48–51. As latching barbs 138 pass over support members 50 and 51, the resilient flexing of arms 132, 134 causes latching barbs 138 to inwardly bias and catch behind support members 50 and 51. The engagement of flat inside surface 142 of each latching barb 138 against the flat side of support members 50 and 51 prevents reinforcing member 116 from unintentionally disconnecting with housing 15. However, in one embodiment arms 132 and 134 are sufficiently flexible that reinforcing member 16 can be removed from housing 11 by simply pulling back on cantilever beam 124. In this regard, reinforcing member 16 is removably positioned.

Figure 5B:
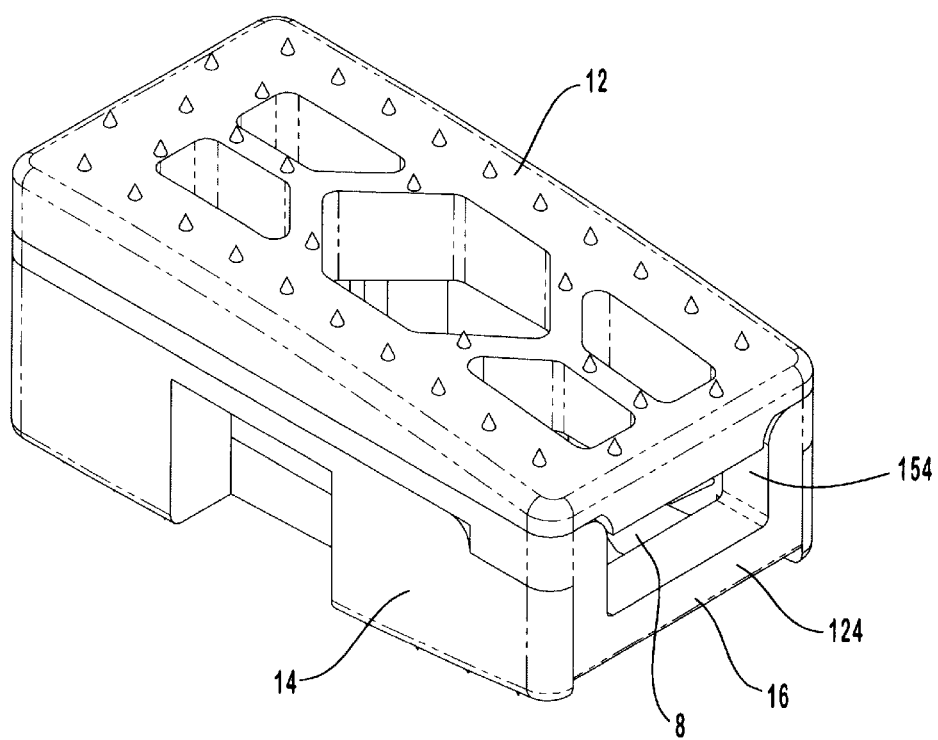
FIG. 5B is a perspective view of the fusion implant shown in FIG. 5A assembled with the reinforcing member.

In the assembled configuration shown in FIG. 5B, reinforcing member 16 is positioned between cap plate 18 and base plate 70. More specifically, any compressive force 122 applied to the assembled fusion implant 10 causes arms 132 and 134 of reinforcing member 16 to be compressed between cap plate 18 and biasing rails 111 and 112. As a result, the compressive load is carried primarily through reinforcing member 16 as opposed to through interlocking teeth 60 and 100. In such configuration, some embodiments of fusion implant 10 are capable of withstanding over 2,000 pounds of compressive force without failure or permanent deformation.

Figure 6A:
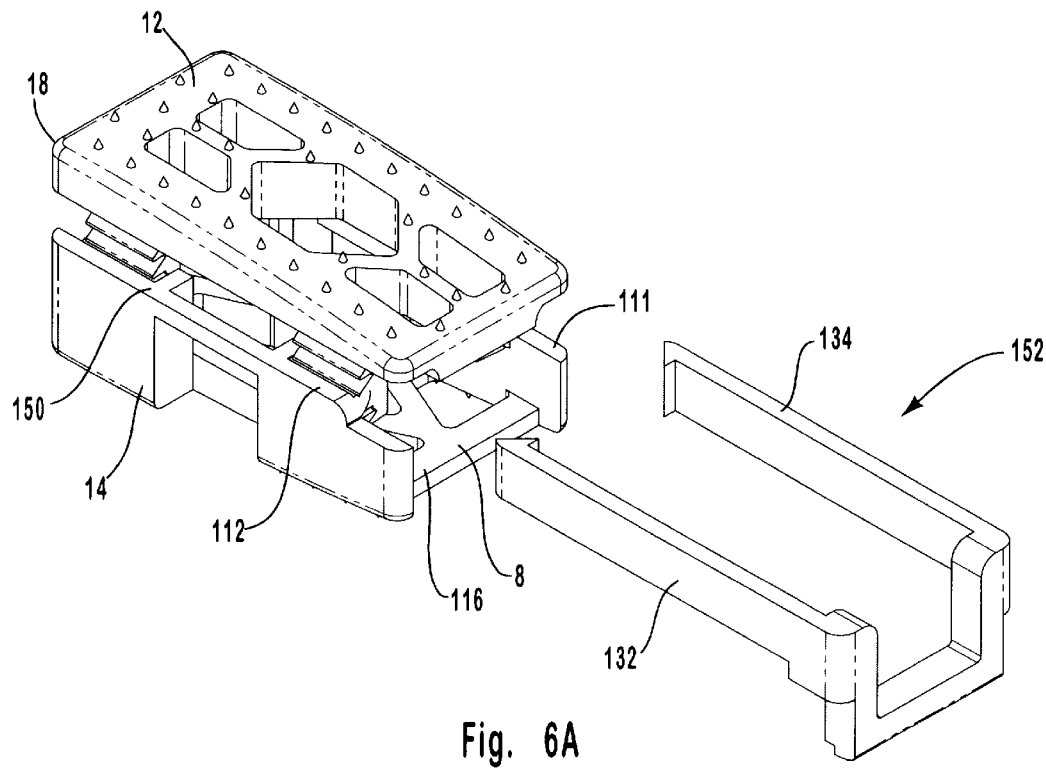
FIG. 6A is a perspective view of the fusion implant shown in FIG. 5A expanded to a greater extent to receive a larger reinforcing member.

As previously discussed, gap size 146 can be selectively incrementally increased by adjusting which teeth 60 and 100 are meshed together. In one embodiment, a discrete reinforcing member is provided for each gap size 146. For example, depicted in FIGS. 5A and 5B, reinforcing member 16 is configured to be received within gap 146 so as to produce a relatively close tolerance. Depicted in FIGS. 6A and 6B, a gap 150 is formed between cap plate 18 and biasing rails 111 and 112. Gap 150 has a height greater than the height of gap 146. For example, gap 146 may correspond to a single tooth spacing while gap 150 corresponds to a spacing of two or more teeth. As such, a reinforcing member 152 is provided. Although reinforcing member 152 has the same structural elements as reinforcing member 16, arms 132 and 134 thereof have an increased height so as to selectively receive within gap 150 under a relatively close tolerance. It is appreciated that a plurality of reinforcing members can be provided with each reinforcing member being configured to fit a different sized gap formed between cap plate 18 and biasing rails 111 and 112. In an alternative embodiment, it is also appreciated that instead of using a larger reinforcing member, a plurality of smaller reinforcing members can be used to fill a single gap. This configuration minimizes the requirement of having to maintain a number of different sizes of reinforcing members.

Figure 6B:
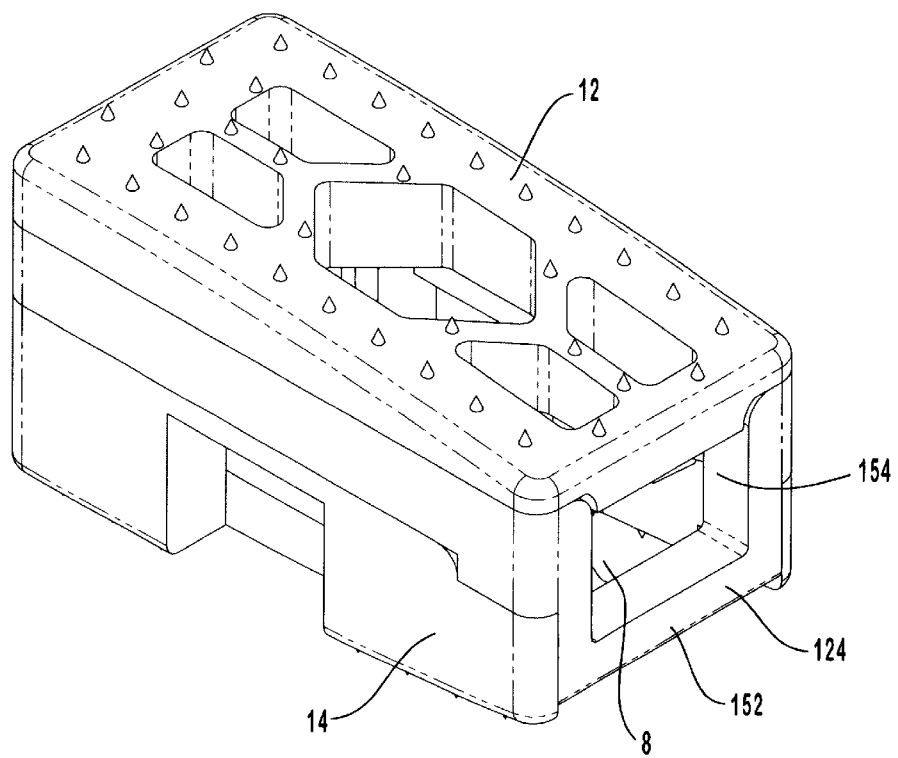
FIG. 6B is a perspective view of the fusion implant shown in FIG. 6A assembled with the larger reinforcing member.

As depicted in FIGS. 5B and 6B, the purpose of using U-shaped cantilever beam 124 is that beam 124 only covers a portion of access mouth 116. An opening 154 remains that provides communication with compartment 8. As discussed below, opening 154 can be used for feeding bone graft into compartment 8.

Figure 6C:
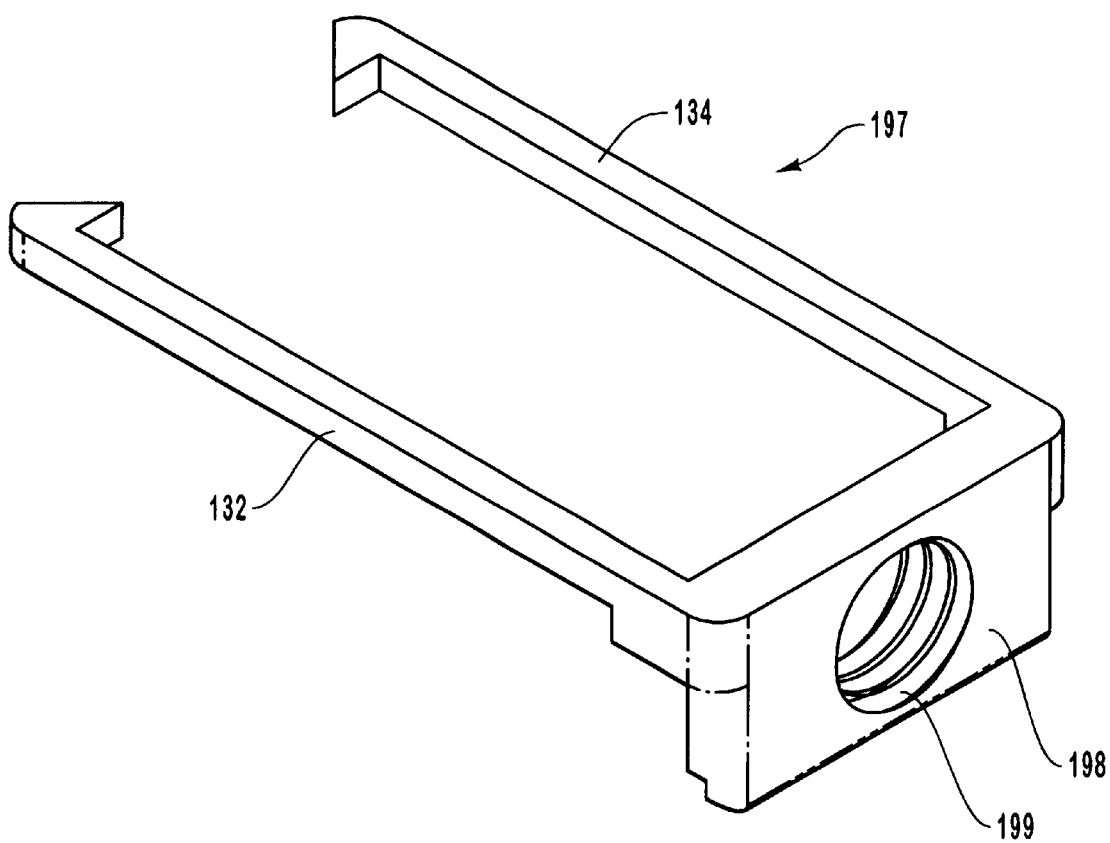
FIG. 6C is a perspective view of an alternative embodiment of a reinforcing member for use with the housing shown in FIG. 5A.

Depicted in FIG. 6C is an alternative embodiment of a reinforcing member 197. Reinforcing member 197 comprises a face plate 198 having arms 132 and 134, as previously discussed, projecting therefrom. In one embodiment of the present invention, means are provided for removably connecting an insertion tool to reinforcing member 197. By way of example and not by limitation, a threaded aperture 199 extends through face plate 198. As will be discussed below in greater detail, threaded aperture 199 enable a tubular insertion tool to be threadedly engaged to aperture 199. The bone graft can then be passed down through the tubular insertion tool and into compartment 8. Examples of alternative embodiments of the means for removably connecting an insertion tool to reinforcing member 197 include the same alternatives as previously discussed with regard to the means for removably connecting an insertion tool to attachment wall 68.

Each of the components of fusion implant 10 is made from a medical grade biocompatible material. In one embodiment, the components are molded from a carbon fiber reinforced polyetheretherketone polymer. In alternative embodiments, the components can be molded, cut, machined, or otherwise formed from medical grade biocompatible metals, polymers, ceramics, or other materials that have adequate strength. It is also appreciated that different components can be made from different materials. For example, the reinforcing member can be made of metal while the remainder is formed from a plastic.

Figure 7A:
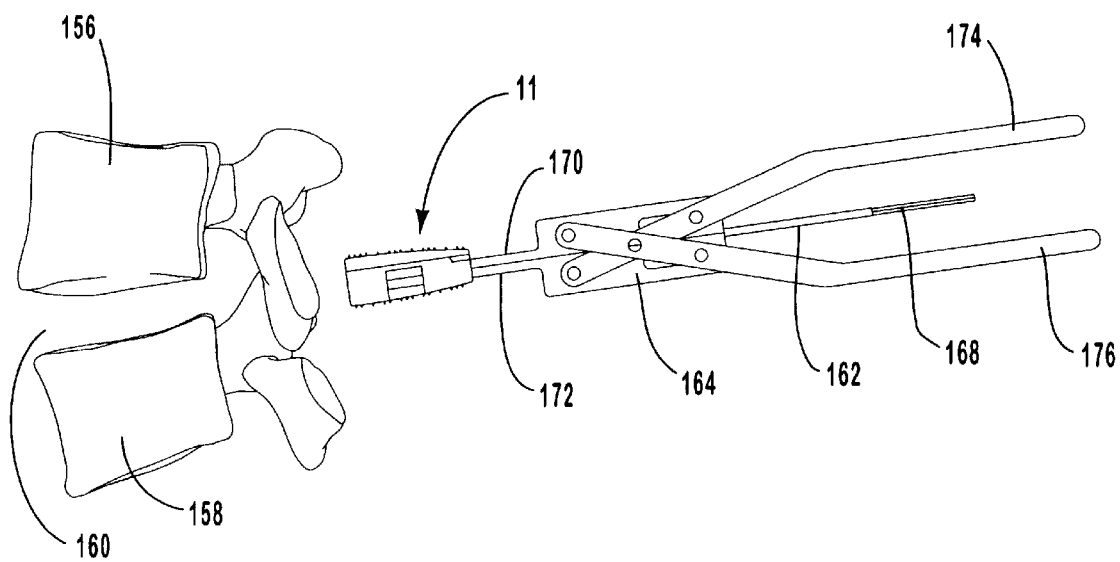
FIG. 7A is a side view of the fusion implant shown in FIG. 3A attached to an inserter and distraction tool before placement between adjacent vertebrae.

Although fusion implant 10 can be used for fusing together a variety of different bone matter together, illustrated below for purposes of example is one method of using fusion implant 10 for fusing together adjacent vertebrae in a spine. Specifically, depicted in FIG. 7A is a pair of adjacent vertebrae 156 and 158. A posterior opening has been made through the back of the person so as to expose vertebrae 156 and 158. A disk or portion of a disk has been removed from between vertebrae 156 and 158 so that a gap 160 is formed therebetween. Because of the select vertebrae, gap 160 is wedged shaped having a wider portion that faces anteriorly towards the front of a patient and is narrower posteriorly towards the back of the patient.

To optimize fusing of vertebrae 156 and 158 while minimizing post-operative complications, a wedged shaped fusion implant having a size substantially corresponding to gap 160 should be inserted within gap 160. Because gap 160 narrows posteriorly, conventional procedures have required that if a wedged shaped implant was to be inserted within gap 160, it would have to be inserted anteriorly through the front of the patient. Inserting through the front of the patient, however, significantly complicates the procedures in that it requires the surgeon to navigate around a number organs and blood vessels. The other conventional option was to insert a flat, i.e., non-wedged shaped, fusion implant posteriorly into gap 160. Since the fusion implant was flat, however, it would not properly fit gap 160, thereby raising the specter of potential post-operative complications. As discussed below, the present invention enables the posterior insertion of a wedged shaped fusion implant into gap 160, thereby optimizing the benefits. Of course, in alternative uses the applicable gap may not be wedged shaped. The fusion implant thus need not be wedged shaped but can be shaped according to its intended use.

Figure 7B:
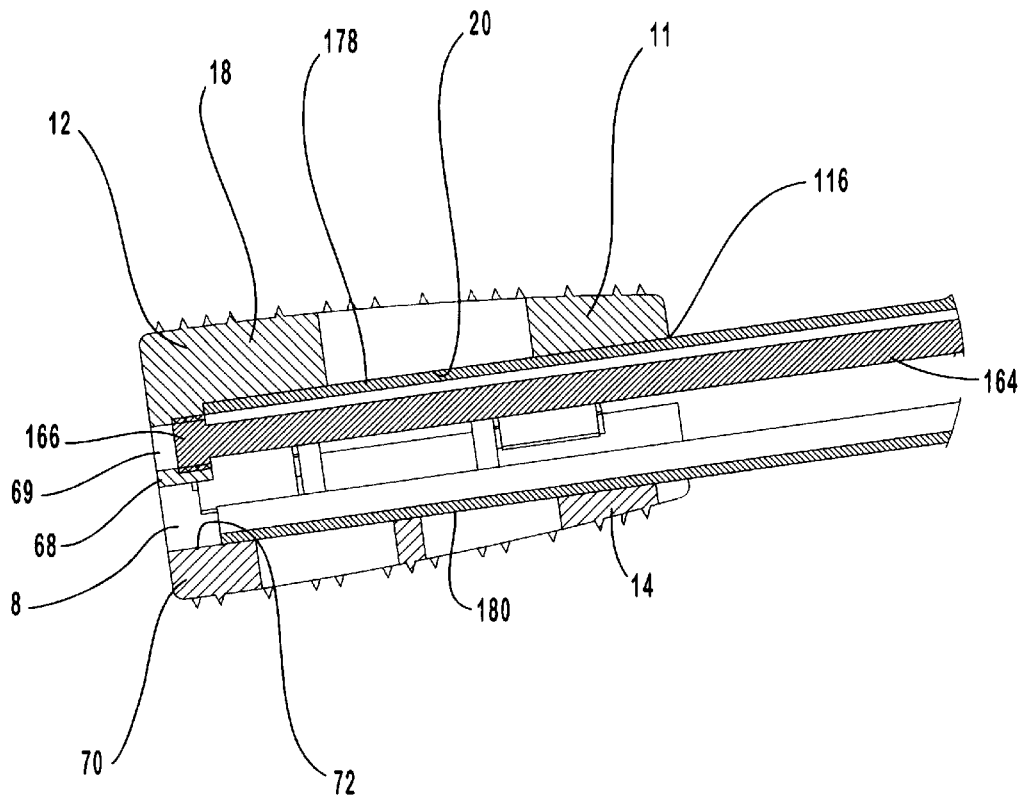
FIG. 7B is an enlarged cross section view of the fusion implant shown in FIG. 7A with the distraction tool being separated.

As depicted in FIGS. 7A and 7B, in one embodiment housing 11 of fusion implant 10 is inserted through the use of an inserter 162 (one form of an insertion tool) and a distraction tool 164. Inserter 162 simply comprises an elongated shaft having a distal end 166 that is inserted into access mouth 116, through compartment 8, and then screwed into threaded aperture 69 in attachment wall 68. Inserter 162 also has a proximal end 168 that is remotely located outside of housing 11. In alternative embodiments, it is appreciated that attachment wall 68 can be connected to base 14. Furthermore, as previously discussed, there are a variety of alternative connection systems and methods that can be used to connect insert 162 to attachment wall 68.

In the embodiment depicted, distraction tool 164 comprises a pair of straight jaws 170 and 172 that are disposed in substantially parallel alignment. Jaws 170 and 172 are hingedly connected to a pair of handles 174 and 176 such that separation of handles 174 and 176 result in substantially constant parallel separation of jaws 170 and 172. As depicted in FIG. 7B, jaws 170 and 172 terminate in a corresponding needle nose 178 and 180, respectively. Needle noses 178 and 180 are inserted through access mouth 116 and into compartment 8 such that needle nose 178 rests against interior face 20 of cap plate 18 and needle nose 180 rests against interior face 72 of base plate 70. (It is noted that for purposes of clarity, distraction tool 164 in FIG. 7B has been expanded as discussed below with regard to FIG. 9.)

Figure 8:
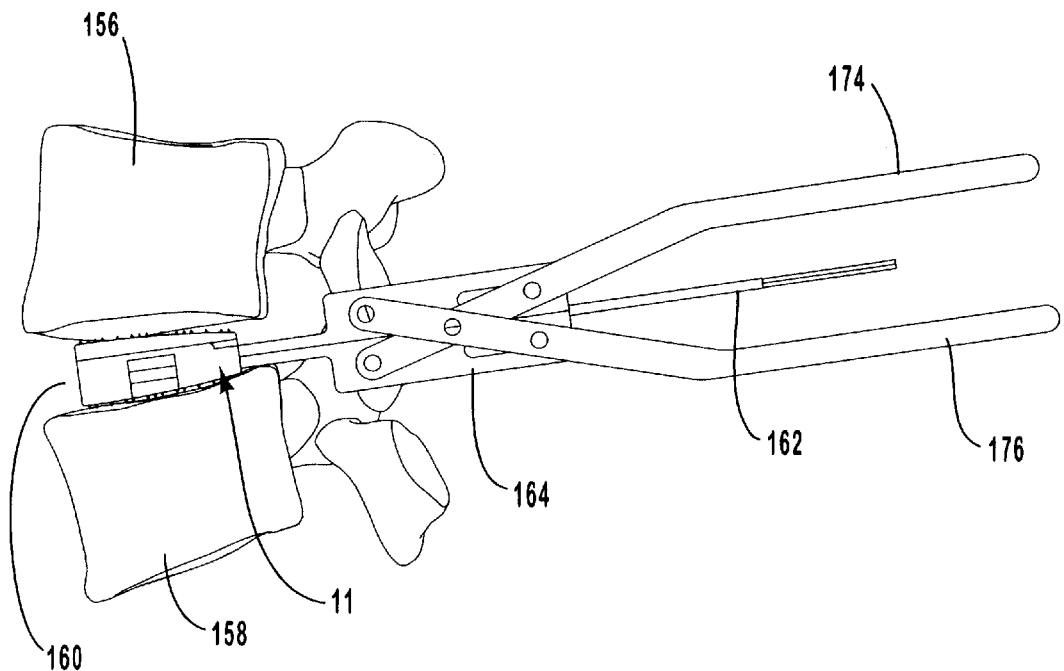
FIG. 8 is a side view of the fusion implant with inserter and distraction tool after placement between adjacent vertebrae.

In this configuration, as depicted in FIG. 8, distraction tool 164 is used to posteriorly insert housing 11 within gap 160. The enlarged distal end of housing 11 is inserted first so that the wedged shaped configuration of the housing 11 matches with the wedged shaped configuration of gap 160. Alternatively, inserter 162 can be used to independently insert housing 11 within gap 160. Once housing 11 is inserted, the end of distraction tool 164 can be inserted within housing 11.

Figure 9:
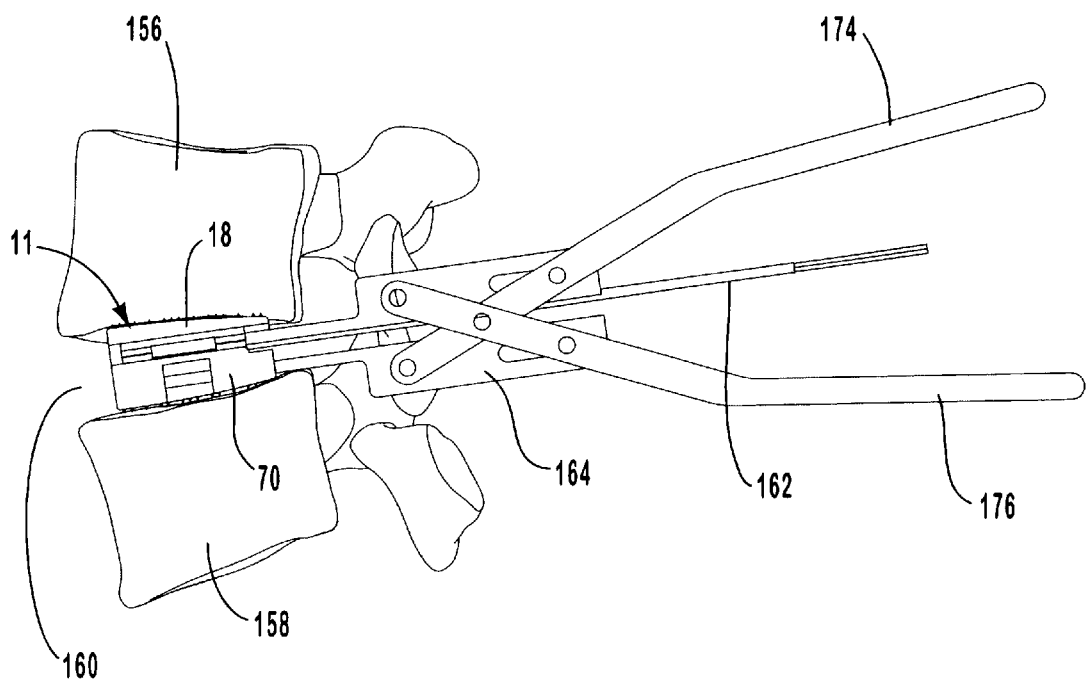
FIG. 9 is a side view of the fusion implant shown in FIG. 8 being expanded by the distraction tool.

As depicted in FIG. 9, once housing 11 is inserted within gap 160, the handles 174 and 176 of distraction tool 164 are expanded such that jaws 170 and 172 are separated. In so doing, housing 11 is also separated, i.e., cap plate 18 is further separated from base plate 70, so that cap plate 18 biases against vertebrae 156 and base plate 70 biases against vertebrae 158. Teeth 60 and 100, as previously discussed, retain housing 11 in the expanded position.

Figure 10:
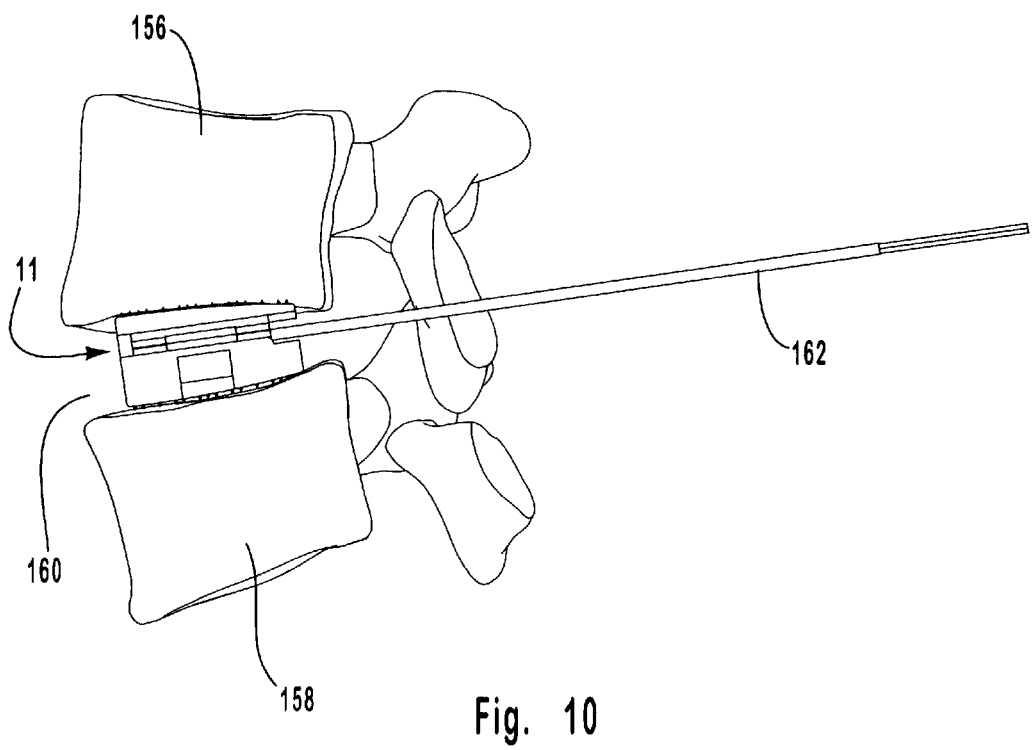
FIG. 10 is the side view of FIG. 9 with the distraction tool removed.

Once housing 11 is expanded within gap 160, distraction tool 164 is collapsed and removed from with housing 11 as depicted in FIG. 10. It is appreciated that distraction 164 can have a variety of different configuration. Virtually any form of tool can be used which can be inserted within compartment 8 and expanded. For example, not only can a number of different forms of pliers be used but other tools which expand by rotation or inflation can also be used.

Figure 11:
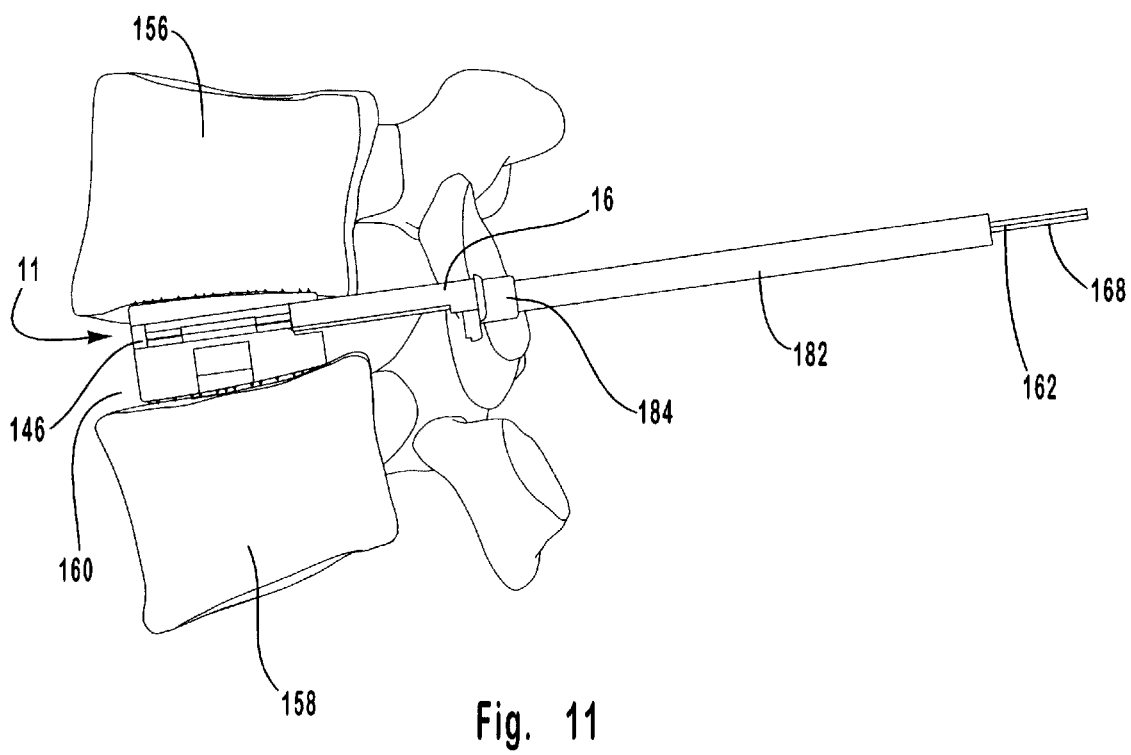
FIG. 11 is the side view of FIG. 10 with the reinforcing member and a push rod coupled to the inserter.
Figure 12:
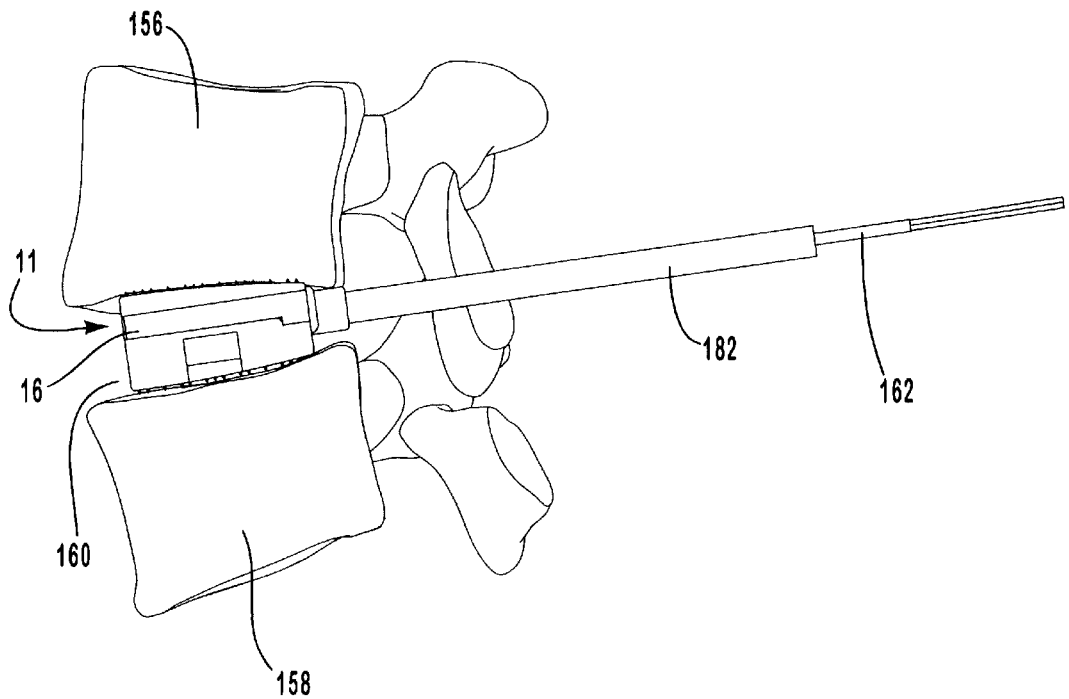
FIG. 12 is the side view of FIG. 11 with the reinforcing member being installed on the fusion implant.

Next, as depicted in FIG. 11, reinforcing member 16 is aligned with gap 146. A tubular push rod 182 is provided having an enlarged head 184. Push rod 182 is passed over the proximal end 168 of inserter 162 such that enlarged end 184 is aligned with reinforcing member 16. In one embodiment, push rod 184 is removably connected to reinforcing member 16 such as by clipping to reinforcing member 16. In this position, push rod 182 is manually advanced over inserter 162 such that push rod 182 advances retention member 16 through gap 146. As a result, retention member 16 is secured to housing 11 as shown in FIG. 12. Alternatively, where reinforcing member 190 is used, the end of push rod 184 can be threaded into threaded aperture 194. In this embodiment, enlarged head 184 is not required.

Figure 13:
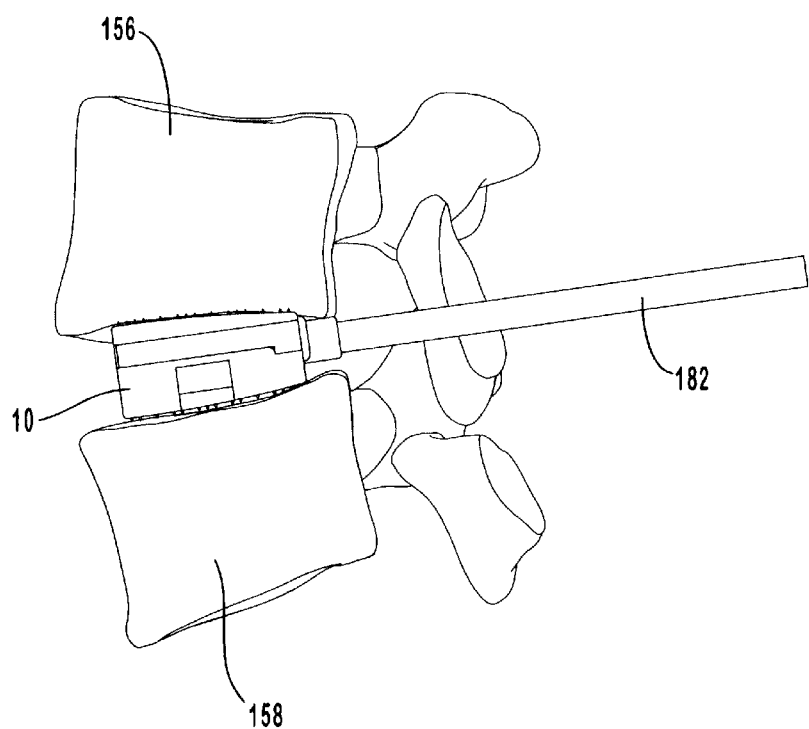
FIG. 13 is the side view of FIG. 12 with the inserter removed.
Figure 14:
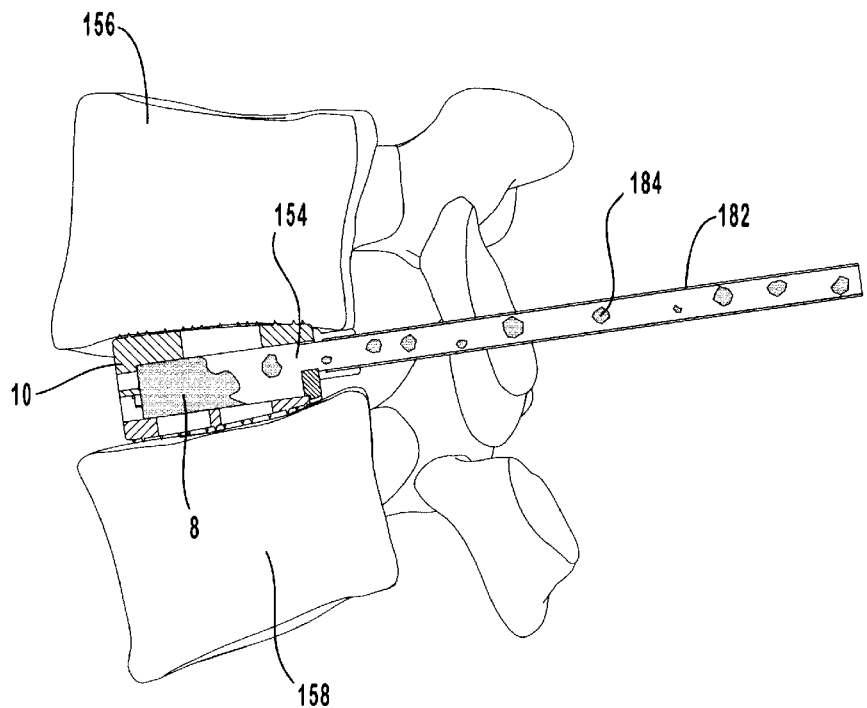
FIG. 14 the side view of FIG. 13 with the push rod in partial cut away showing the delivery of osteogenic material.
Figure 15:
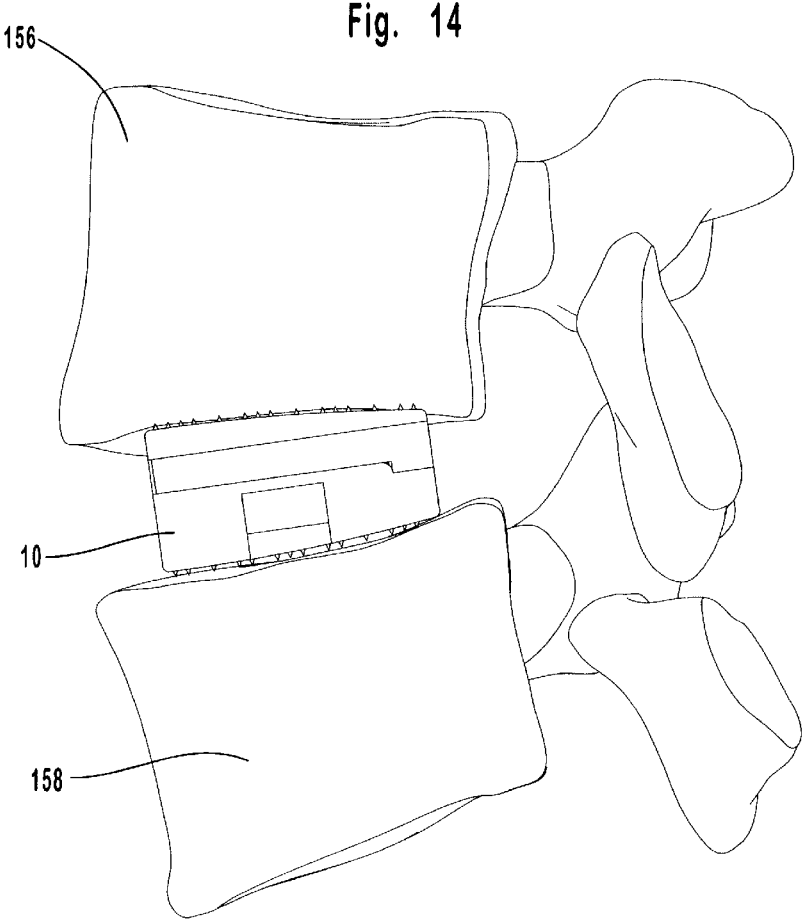
FIG. 15 is a side view of the assembled fusion implant installed in the intervertebral space.

Next, inserter 162 is unscrewed from attachment wall 68 and withdrawn out of tubular push rod 182 as shown in FIG. 13. As depicted in FIG. 14, tubular push rod 182 is now in fluid communication with compartment 8 through opening 154 or, where reinforcing member 190 is used, through threaded aperture 194. As such, an osteogenic substance 184, such as bone graft, is passed down through push rod 182 so as to pack compartment 8 therewith. In other uses, it is also appreciated that compartment 8 can be at least partially packed with an osteogenic substance prior to insertion into the patient. Once compartment 8 is sufficiently packed with osteogenic substance 184, push rod 182 is removed as depicted in FIG. 15. Alternatively, a cap (not shown) may be delivered through push rod 182 and installed on reinforcing member 16 or within opening 154 so as to better contain osteogenic substance 184 within compartment 8.

The above process is for inserting fusion implant 10 within gap 160 on one side of a spinal cord. If required, the same above process can then be repeated for inserting another fusion implant 10 within gap 160 on the opposing side of the spinal cord.

Figure 16A:
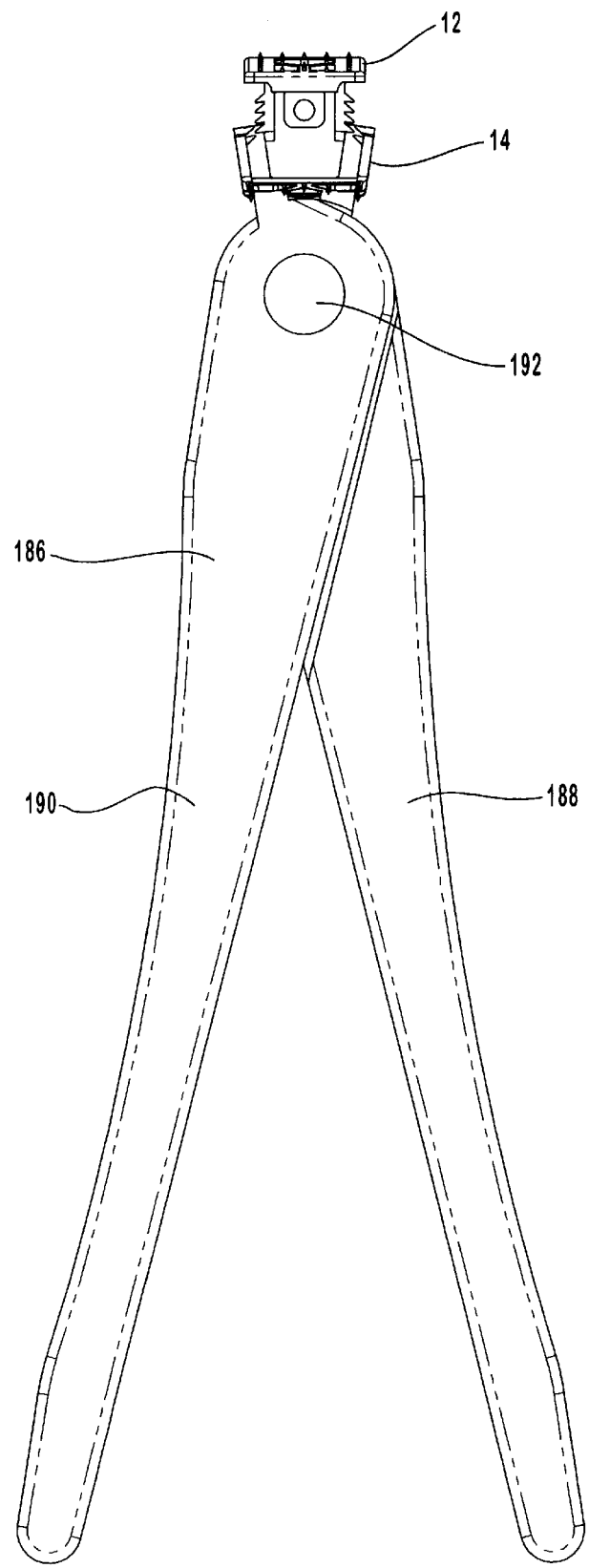
FIGS. 16A and 16B are elevated side views of expansion pliers expanding a base of the fusion implant shown in FIG. 1 for receiving a cap thereof.
Figure 16B:
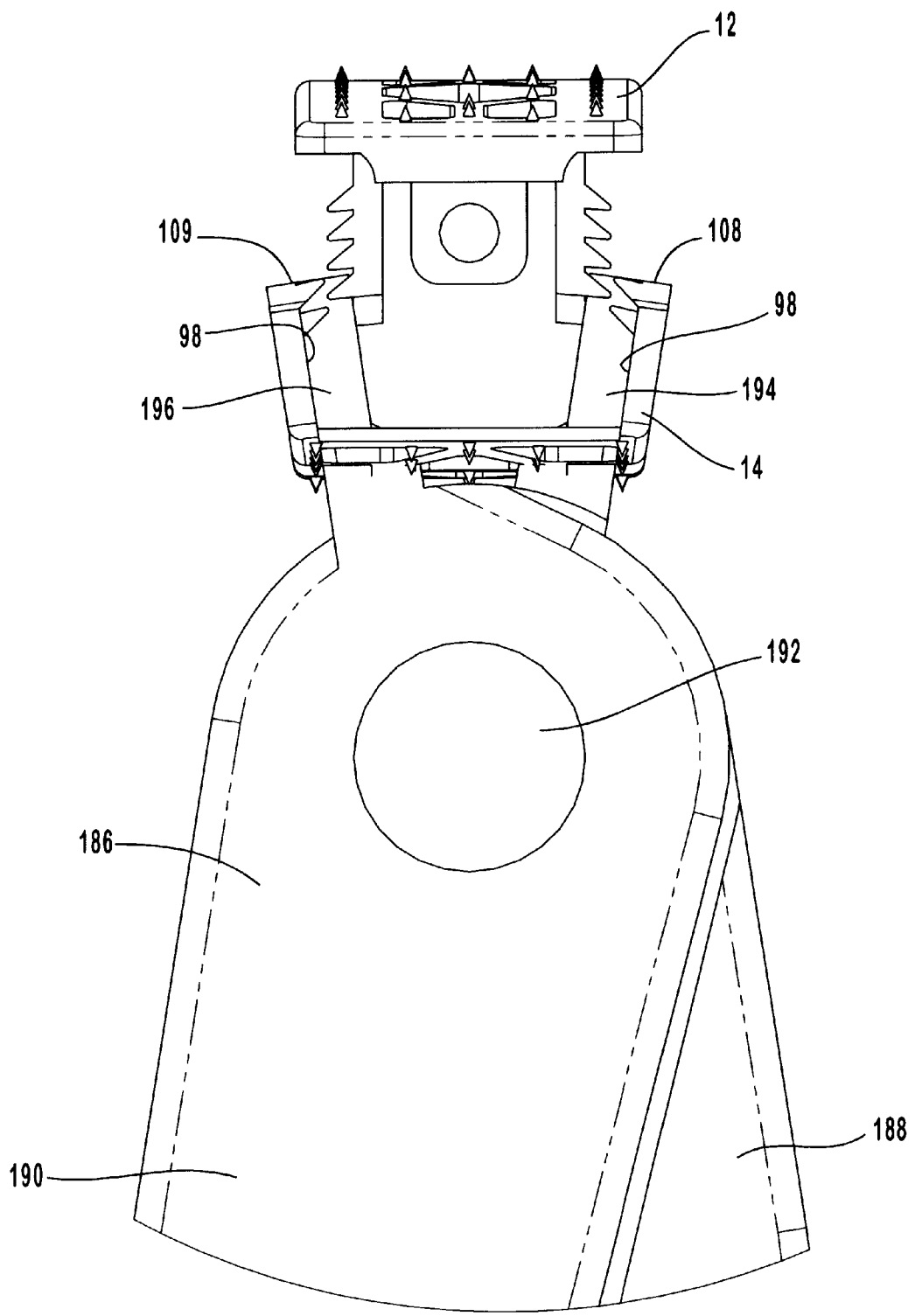

Depicted in FIGS. 16A and 16B is one method for initially attaching cap 12 to base 14. As depicted therein, expansion pliers 186 are provided comprising a pair of handles 188 and 190 that are secured together at a hinge 192. A narrow prong 194 and 196 projects from handles 188 and 190, respectively, at hinge 192. The prongs are positioned such that as handles 188 and 190 are separated, prongs 194 and 196 are also separated.

As previously discussed with regard to FIG. 2, a vertical channel 101 is formed on each side of base 14. Each vertical channel 101 extends to a location inward of braces 108 and 109. Depicted in FIGS. 16A and 16B, prongs 194 and 196 have each been received within a corresponding vertical channel 101 so that the top end of prong 194 and 196 is positioned inward of brace 108 and 109, respectively. Handles 188 and 190 have been separated so as to separate prongs 194 and 196. As prongs 194 and 196 were separated, the prongs biased against braces 108 and 109, thereby causing support members 86–89 with teeth 100 thereon to outwardly flex.

With teeth 100 outwardly flexed, support members 48–51 of cap 12 can be freely disposed inward of support members 86–89 of base 14. Expansion pliers 186 can then be collapsed and removed, thereby causing support members 48–51 to engage with corresponding support members 86–89 as previously discussed.

Figure 17:
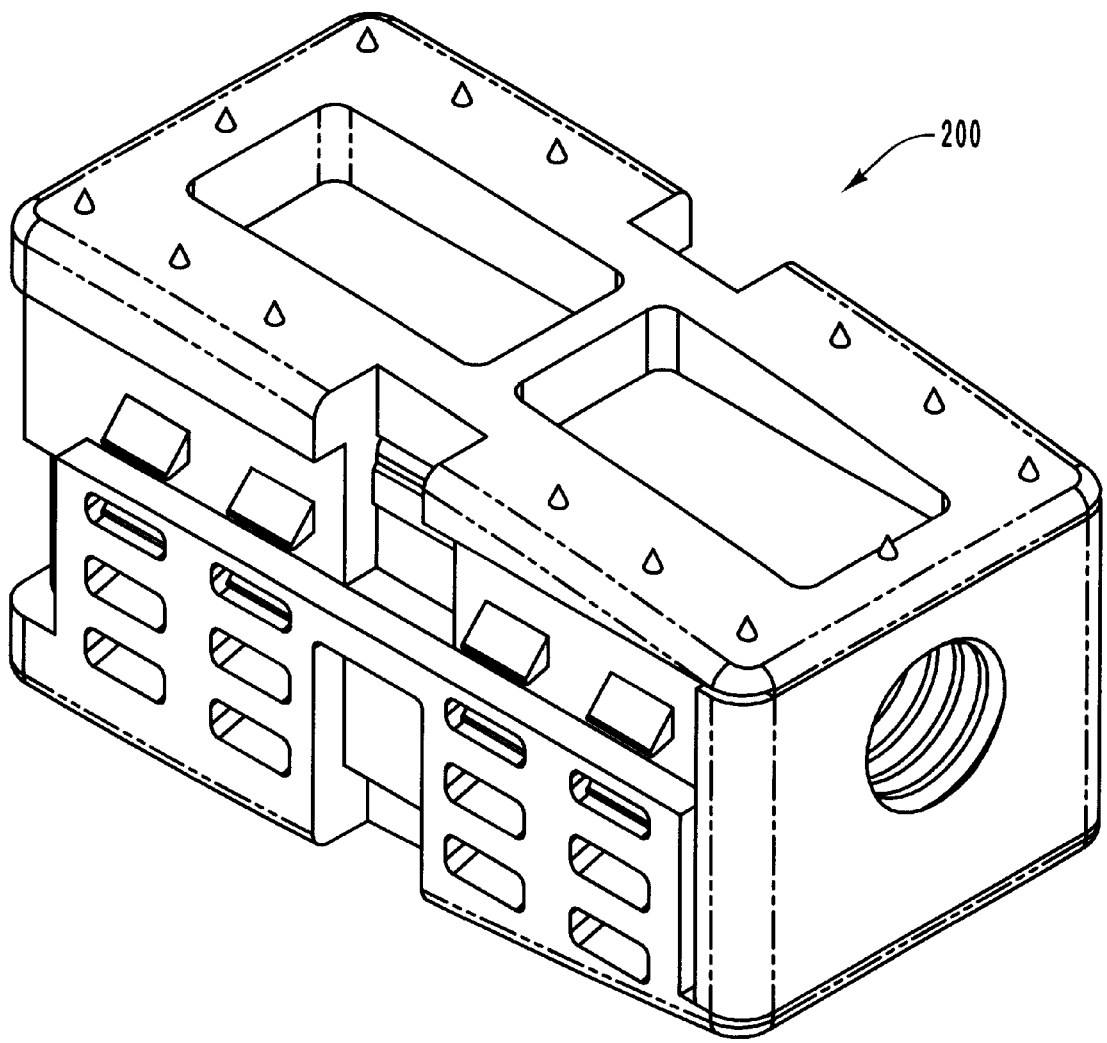
FIG. 17 is a perspective view of an alternative embodiment of an adjustable bone fusion implant in an assembled state.
Figure 18:
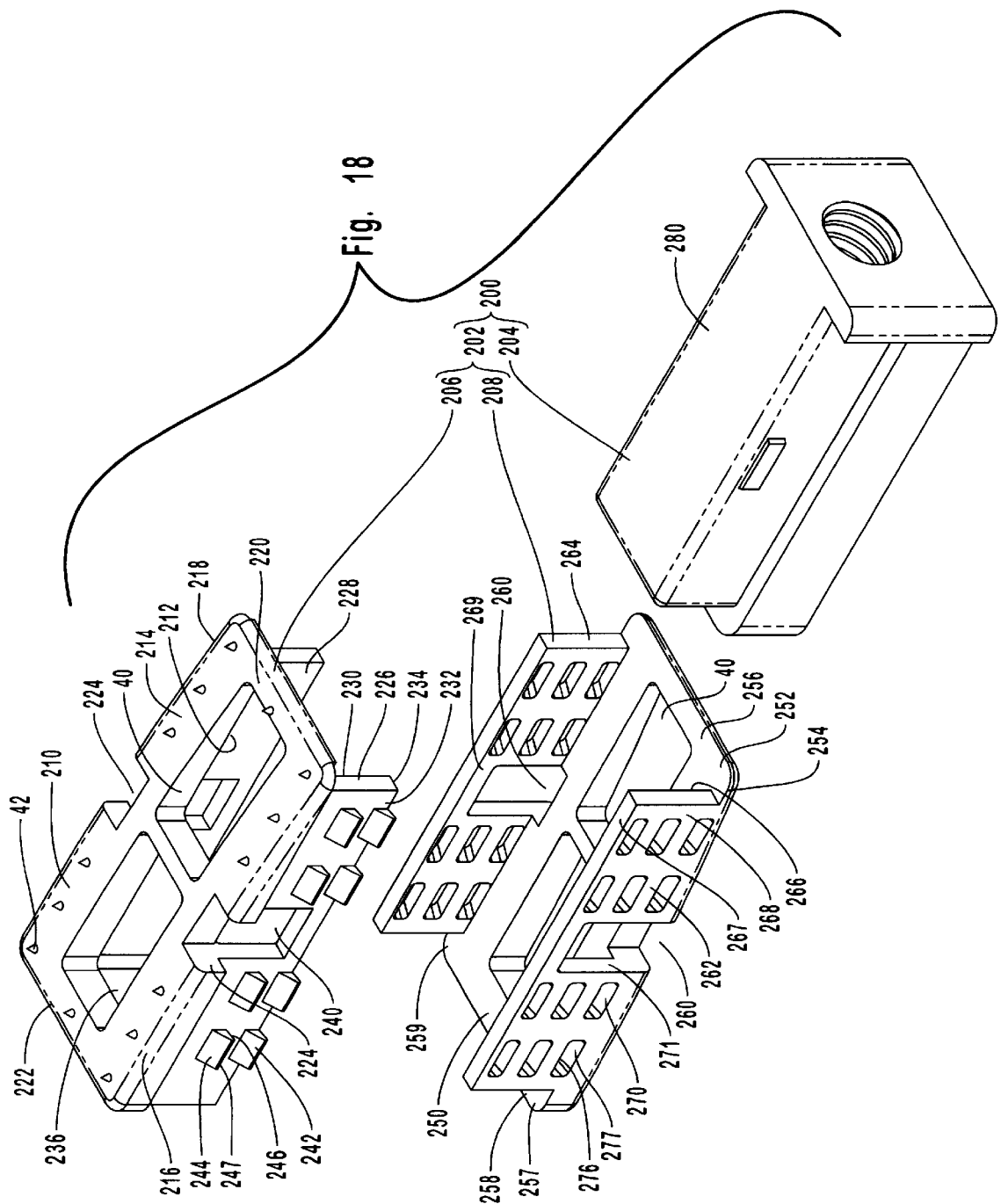
FIG. 18 is a perspective view of the embodiment shown in FIG. 17 in a disassembled state.

Depicted in FIG. 17 is an alternative embodiment of an adjustable bone fusion implant 200. Fusion implant 200 functions in a manner similar to previously discussed fusion implant 10. Specifically, as depicted in FIG. 18, fusion implant 200 comprises a housing 202 and a reinforcing member 204. In turn, housing 202 comprises a cap 206 that is selectively connected to a base 208.

Cap 206 comprises a cap plate 210 that is substantially the same as cap plate 18 of fusion implant 10. Specifically, cap plate 210 has an interior face 212 and an opposing exterior face 214 each extending between a proximal end 220 and an opposing distal end 222 and between opposing sides 216 and 218. A notch 224 is centrally disposed and recessed into each side 216 and 218.

Interior and exterior faces 212 and 214 can be sloped, parallel or have other orientations as discussed with regard to cap plate 18. Furthermore, extending through cap plate 210 from exterior face 214 to interior face 212 are a pair of grafting ports 40. Grafting ports 40 can have the same alternative configurations, sizes, and orientations as previously discussed with regard to grafting ports 40 on fusion implant 10. Upwardly projecting from exterior face 214 of cap plate 210 are a plurality of retention barbs 42. Retention barbs 42 can also have the same alternative configurations and orientations as previously discussed with regard to fusion implant 10.

A first support member 226 and a second support member 228 downwardly project from interior face 212 of cap plate 210 along side 216 and side 218, respectively. Each support member 226 has an inside face 230 and an outside face 232 that project to an exposed end face 234. Extending through each support member 226 and 228 in alignment with corresponding notch 224 is a side port 240. In part, each side port 240 functions as a grafting port. Outwardly projecting form outside face 232 of each support member 226, 228 are a plurality of both laterally and vertically spaced apart teeth 242. As will be discussed below in greater detail, each tooth 242 has a top surface 244 and a bottom surface 246 which intersect at an outside edge 247.

Figure 21:
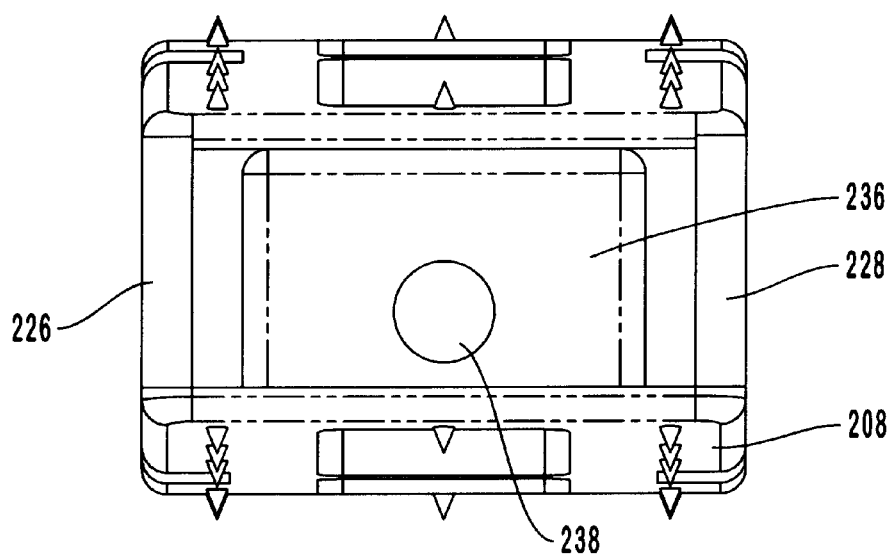
FIG. 21 is an elevated front end view of the housing shown in FIG. 19 in a fully collapsed state.
Figure 22:
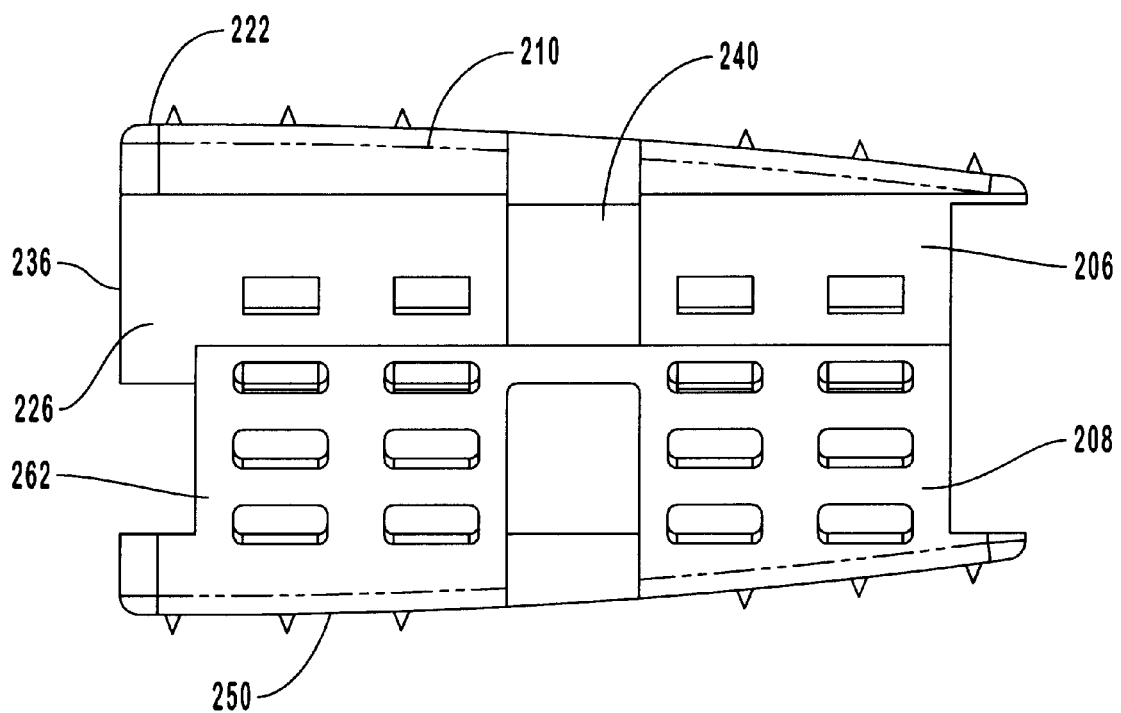
FIG. 22 is an elevated side view of the housing shown in FIG. 19 in a fully expanded state.

As perhaps best depicted in FIGS. 18, 21, and 22, an attachment wall 236 downwardly projects from distal end 222 of cap plate 210. The opposing ends of attachment wall 236 connect with the proximal end of each support member 226 and 228. In alternative embodiments, as with attachment wall 68 of fusion implant 10, attachment wall 236 can be spaced apart from support members 226 and 228. Attachment wall 236 can also be formed as part of base 208. As also with fusion implant 10, means are provided for removably connecting an insertion tool to attachment wall 236. By way of example and not by limitation, extending through attachment wall 236 is a threaded aperture 238. Threaded aperture 238 enables housing 202 to be threadedly connected to previously discussed inserter 162.

Returning to FIG. 18, base 208 includes a base plate 250 that is substantially the same as cap plate 210. That is, base plate 250 includes an interior face 252 and an opposing exterior face 254 that each extend between a proximal end 256 and an opposing distal end 258 and between opposing sides 257 and 259. A notch 260 is centrally disposed and recessed into each side 257 and 259. Extending through base plate 250 are a plurality of grafting ports 40. A plurality of retention barbs 42 outwardly projecting from exterior face 254. The alternatives as discussed above with regard to cap plate 210 are also applicable base plate 250.

A third support member 262 and a fourth support member 264 upwardly project from interior face 252 of base plate 250 along side 257 and side 259, respectively. Each support member 262 and 264 has an inside face 266 and an opposing outside face 268 that each project to an exposed end face 267. Extending through each support member 262 and 264 in alignment with a corresponding notch 260 is a side port 271. Each support member 262 and 264 includes a brace portion 269 that extends across side port 271.

Figure 19:
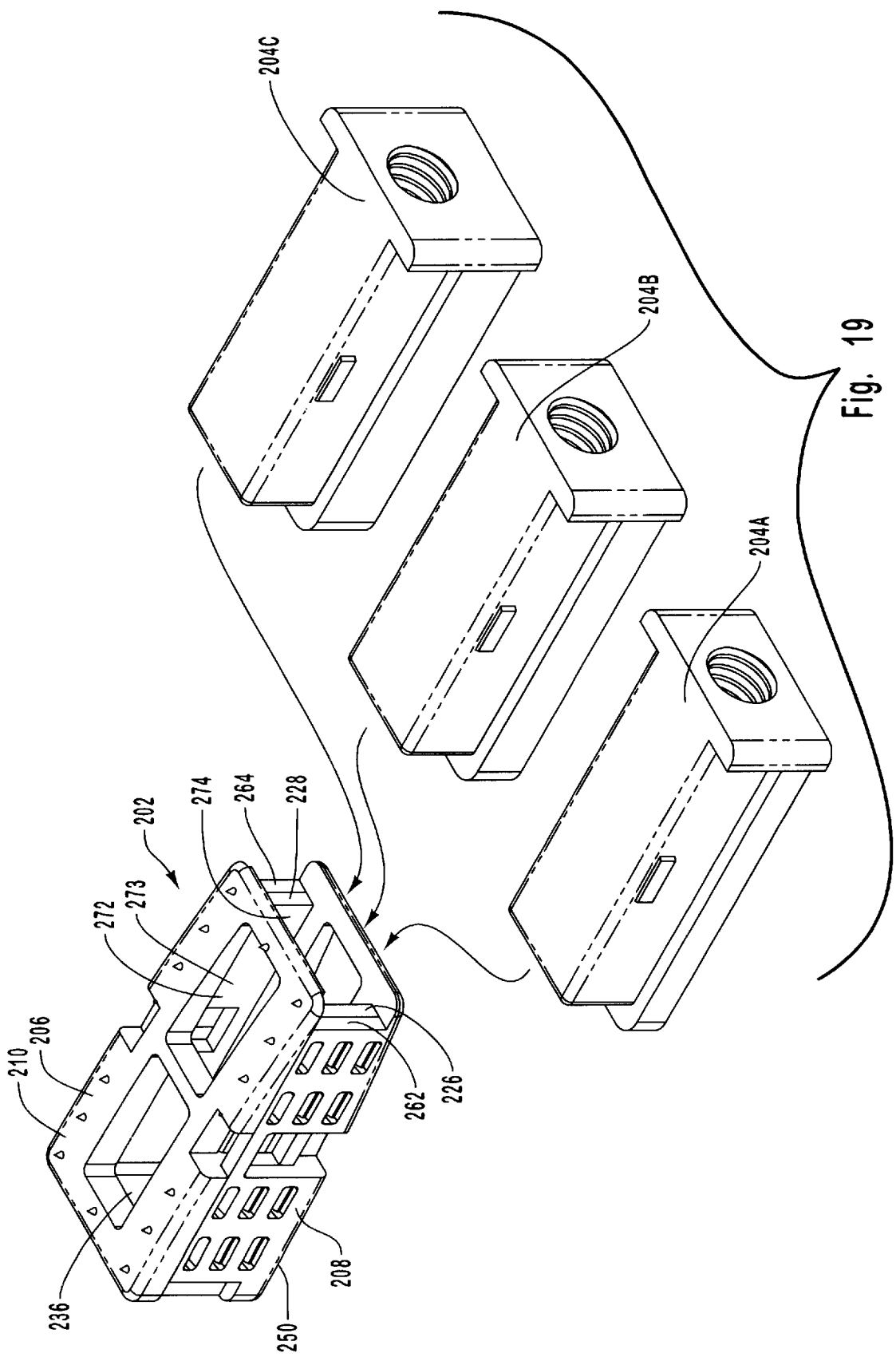
FIG. 19 is a perspective view of the assembled housing of the embodiment shown in FIG. 17 with a plurality of alternatively sized reinforcing members spaced apart therefrom.

Extending through each support member 262 and 264 are a plurality of vertically and horizontally spaced apart elongated adjustment holes 270. Each hole 270 has a substantially flat top surface 276 and a substantially flat bottom surface 277. Cap 206 is configured to adjustable mate with base 208 so that select teeth 242 of cap 206 are received within select adjustment holes 270 of base 208. Specifically, in substantially the same way as previously discussed with regard to fusion implant 10, expansion pliers 186 as depicted in FIGS. 16A and 16B, or some other similarly operable tool, can be inserted in opposing side ports 271 of base 208 to facilitate outward resilient expansion of support members 262 and 264. Cap 206 can then be inserted between support members 262 and 264 such that when expansion pliers 186 are removed, teeth 242 of cap 206 are received within select adjustment holes 270 of base 208. In this assembled configuration, as shown in FIG. 19, housing 202 is in a assembled collapsed state.

Viewed as a whole, housing 202 has an interior surface 272 that at least partially bounds a compartment 273. Specifically, compartment 273 is bounded by cap plate 210, base plate 250, attachment wall 236 and between the support members 226, 228, 262, and 264. An access mouth 274 formed at the proximal end of housing 202 provides open access to compartment 273.

As with housing 11 of fusion implant 10, housing 202 can also be selectively expanded so as to form compartment 273 into one of a plurality of predefined sizes. Specifically, as a separation force is applied to cap 206 and base 208 in the directions indicated by arrows 120 in FIG. 20, top surface 244 of teeth 242 bias against top surface 276 of corresponding adjustment holes 270 creating an inward flexing movement of support members 226 and 228 on cap 206 and/or an outward flexing movement of support members 262 and 264 on base 208. This flexing of the support members enables teeth 242 to pass from one hole 270 into the next adjacent vertical hole. As a result, housing 202, and thus compartment 273, can be selectively expanded by predefined incremental amounts. The incremental amounts are based on the spacing of teeth 242 and holes 270. To facilitate ease in the flexing of the support member, top surface 244 of teeth 242 is typically sloped so as to form an inside angle $\theta_1$ relative to the exterior face of the support members in a range between about 15 degrees to about 45 degrees with about 25 degrees to about 35 degrees being more common.

Figure 20:
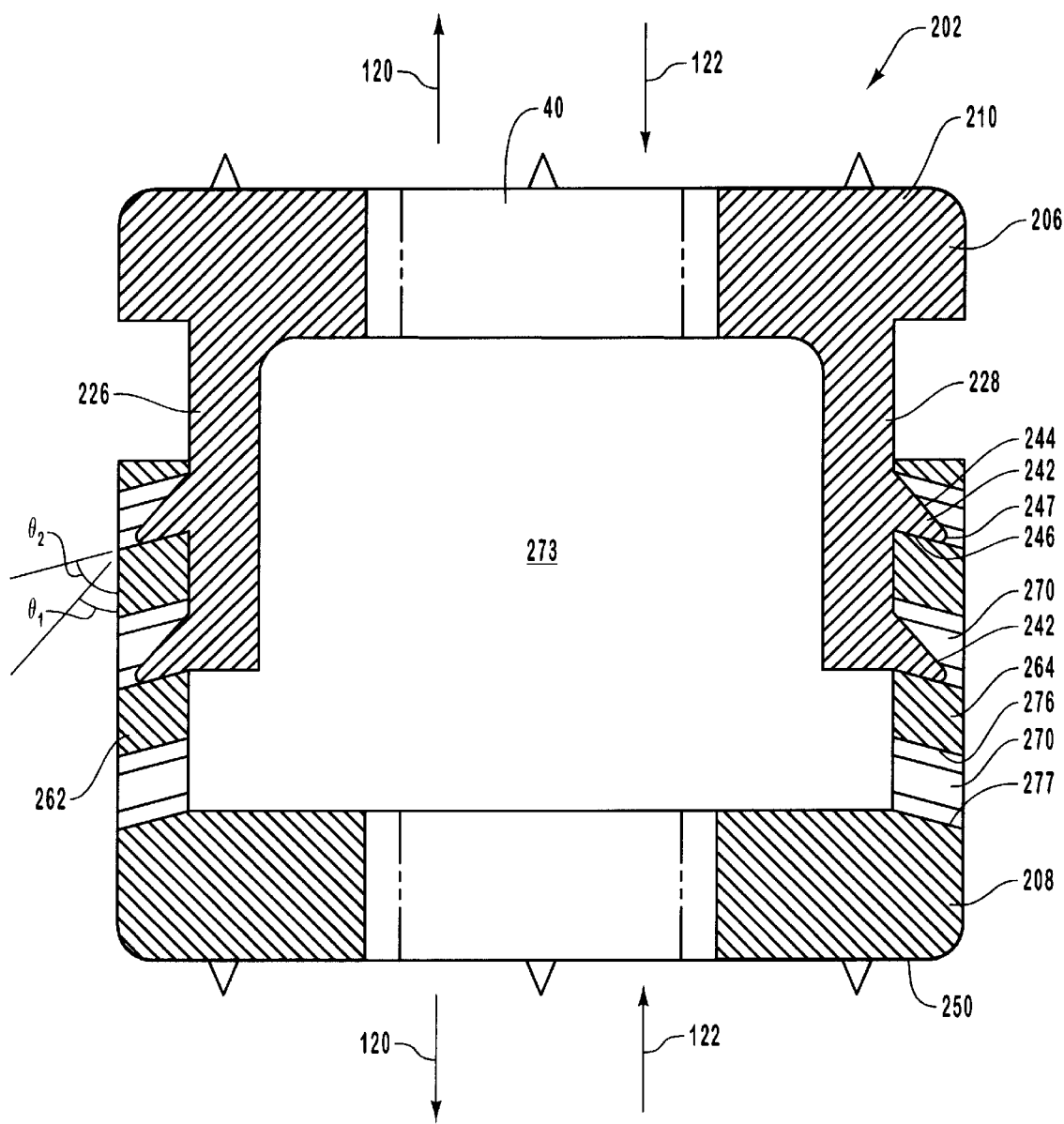
FIG. 20 is a cross section front view of the housing shown in FIG. 19 in a partially expanded state.

In contrast, as a compression force is applied to cap 206 and base 208 in the directions indicated by arrows 122 depicted in FIG. 20, bottom surface 246 of teeth 242 press against bottom surface 277 of corresponding adjustment holes 270 so as to form a mechanical stop that precludes the collapse of housing 202. In the embodiment depicted, bottom surface 246 of teeth 242 and bottom surface 277 of adjustment holes 270 are complementary sloped so as to form an inside angle $\theta_2$ relative to the exterior face of the support members in a range between about 60 degrees to about 90 degrees with about 70 degrees to about 80 degrees being more common. In an alternative embodiment, the bottom surface of teeth 242 and holes 270 can be horizontally disposed. Having them complementary sloped, however, helps to ensure that teeth 242 do not accidentally slip out of holes 270 when under compression.

The combination of support members 226 and 262 and/or the combination of support member 228 and 264 is another example of an expandable sidewall and is also another example of the means for connecting the cap plate to the base plate such that the cap plate and the base plate can be selectively manually separated to one or more predefined positions and such that the cap plate and the base plate are mechanically stopped from collapsing toward each other once separated to the one or more predefined positions. In other embodiments, it is appreciated that adjustment holes 270 need not extend all the way through support members 262 and 264. Furthermore, some or all of the teeth 242 and holes 270 can be switched between the various support member. In addition, teeth 242 and holes 270 can have any desired configuration as long as they perform the desired function.

Figure 23:
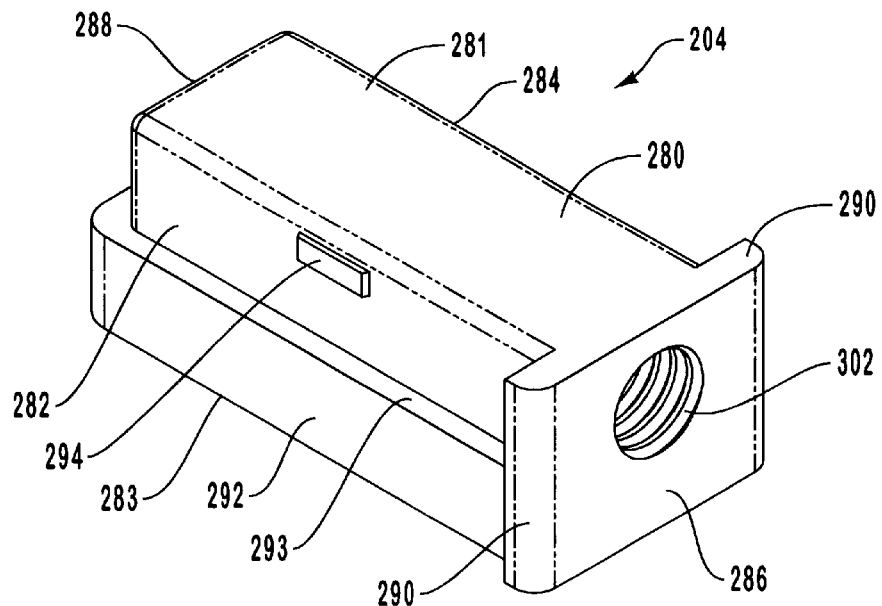
FIG. 23 is a front perspective view of a reinforcing member shown in FIG. 19.
Figure 24:
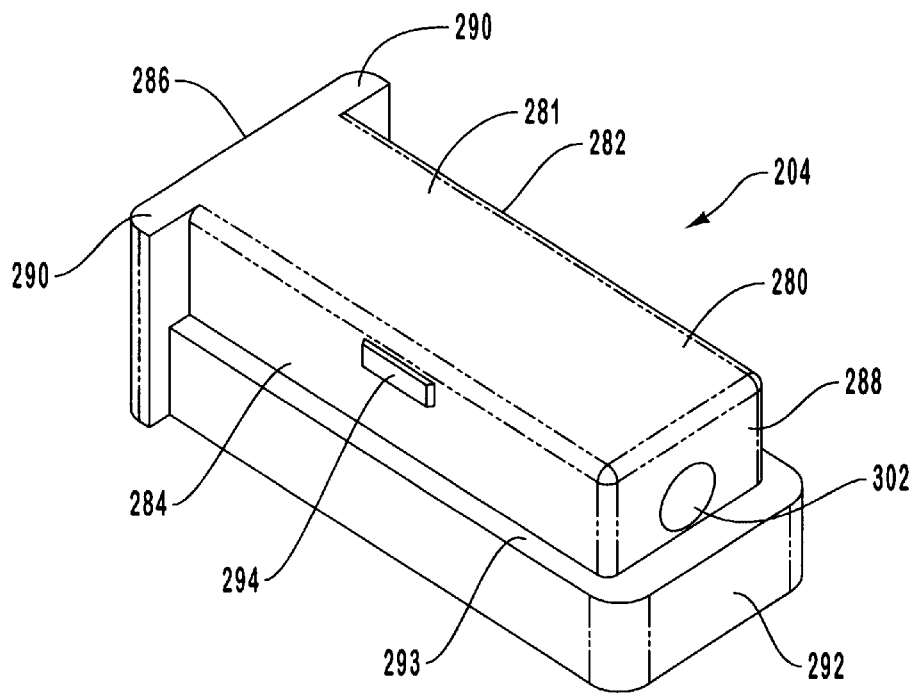
FIG. 24 is a rear perspective view of the reinforcing member shown in FIG. 23.

Returning to FIG. 18, reinforcing member 204 comprises a substantially rectangular block body 280. As depicted in FIGS. 23 and 24, block body 280 includes a top face 281, a bottom face 283, and a pair of opposing side faces 282 and 284 that extend between a proximal end face 286 and an opposing distal face 288. A flange 290 projects from each side face 282 and 284 adjacent to proximal end face 286. A support shelf 292 outwardly projects from block body 280 along side faces 282, 284, and distal end face 288. Support shelf 292 extends from bottom face 283 of block body 280 to an exposed bearing face 293 positioned part way to top surface 281. Outwardly projecting from each side face 282 and 284 of block body 280 above bearing face 293 is a detent 294.

Figure 25:
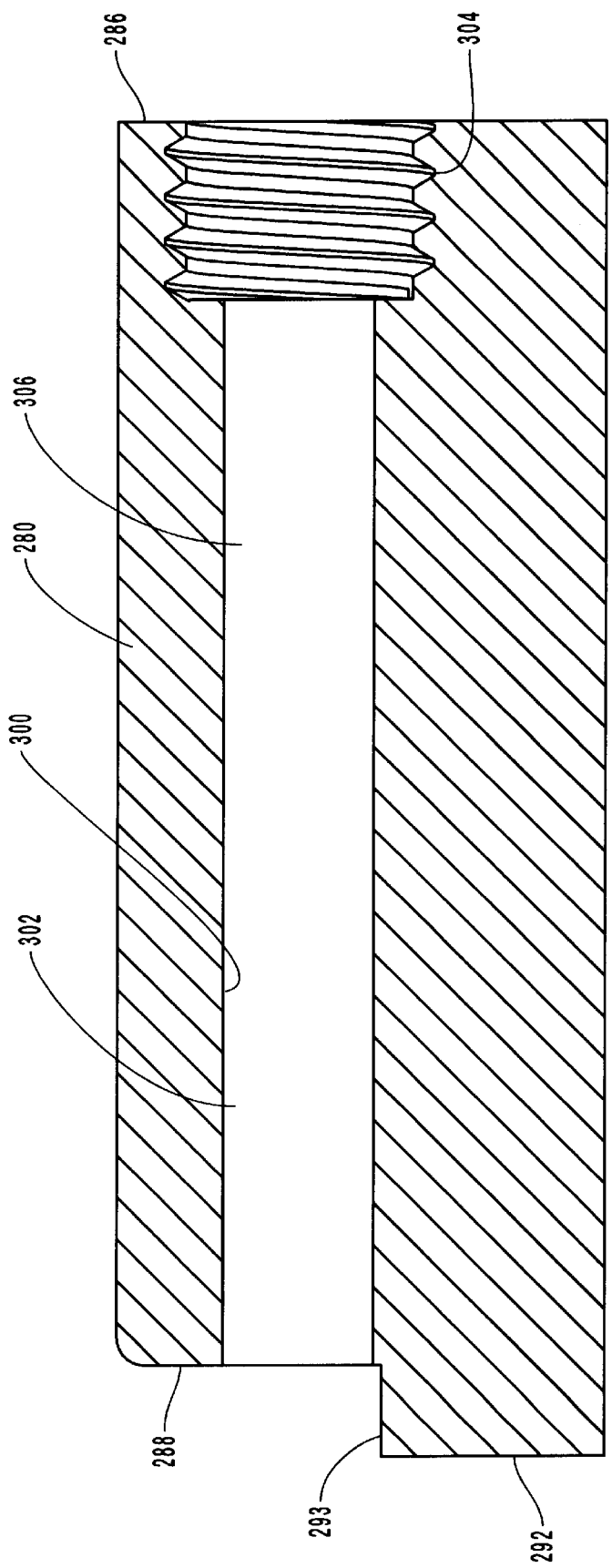
FIG. 25 is a cross sectional side view of the reinforcing member shown in FIG. 23.

As depicted in FIG. 25, block body 280 has an interior surface 300 that bounds a passageway 302 extending between proximal end face 286 and distal end face 288. Passageway 302 includes a threaded portion 304 that begins at proximal end face 286 and a smooth surface portion 306 that extends from threaded portion 304 to distal end face 288. Thread portion 304 comprises one example of means for removably connecting an insertion tool to reinforcing member 204.

Figure 26:
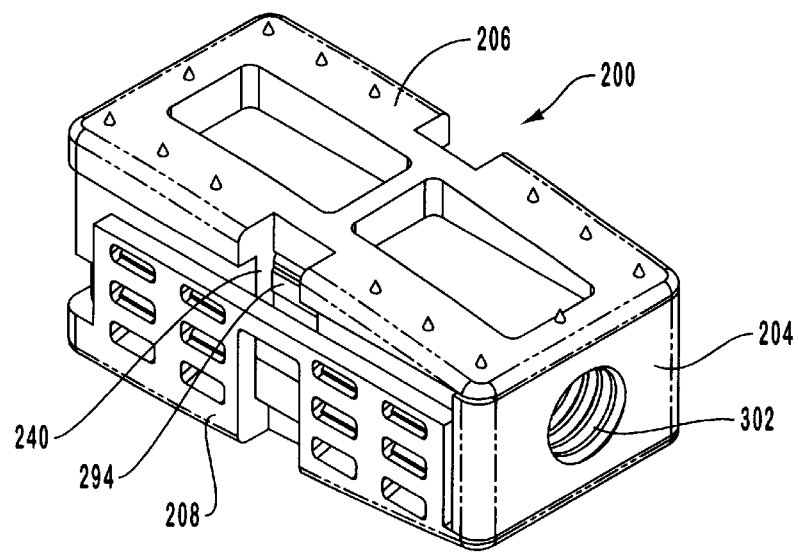
FIG. 26 is a perspective view of the housing shown in FIG. 19 having a reinforcing member inserted therein forming a fusion implant.

Returning to FIG. 19, depending on the size of compartment 273, i.e., depending on whether housing 202 is fully collapsed or in the one or more expanded configurations, one of a plurality of different sized reinforcing members 204A–C can be selectively and removably slid within compartment 310 through access mouth 274. One such fully assembled embodiment is depicted in FIG. 26. As shown therein, when reinforcing member 204 is received within compartment 273, each detent 294 on reinforcing member 204 projects into a corresponding side port 240 of cap 206. Although not required, detents 294 help to ensure that reinforcing member 204 does not unintentionally slide out of compartment 273. Even with detents 294 present, however, reinforcing member 204 can be removed, if desired, by pulling on reinforcing member 204 as discussed below. As such, reinforcing member 204 is removably positioned within compartment 273.

Figure 27:
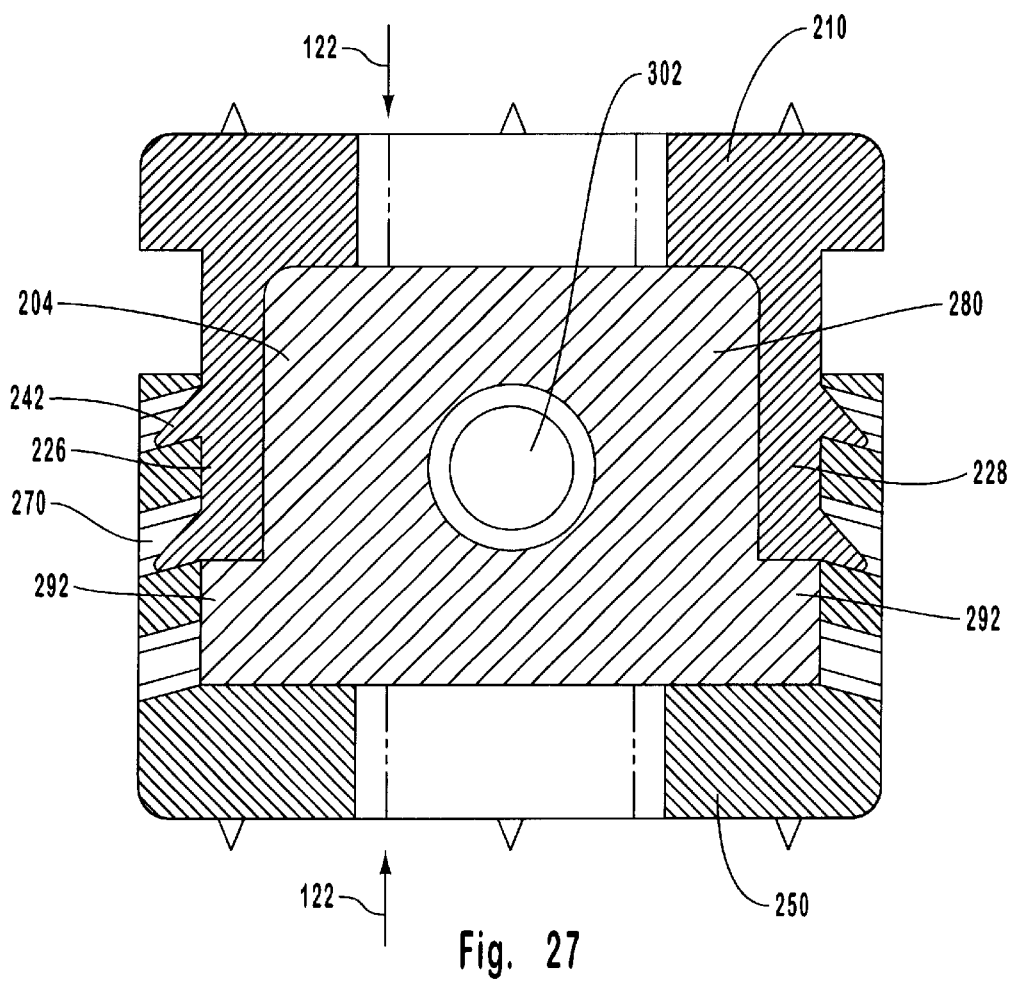
FIG. 27 is a cross sectional front view of the fusion implant shown in FIG. 26.

Turning to FIG. 27, when in the fully assembled configuration, block body 280 of reinforcing member 204 is compressed between the interior faces of cap plate 210 and base plate 250 when compressive force 122 is applied. Similarly, support shelf 292 is compressed between support members 226, 228 and base plate 250. As such, when reinforcing member 204 is inserted within compartment 273 and compressive force 122 is applied to fusion implant 200, compressive force 122 is primarily carried through reinforcing member 204 as opposed to between teeth 242 and adjustment holes 270.

Figure 28:
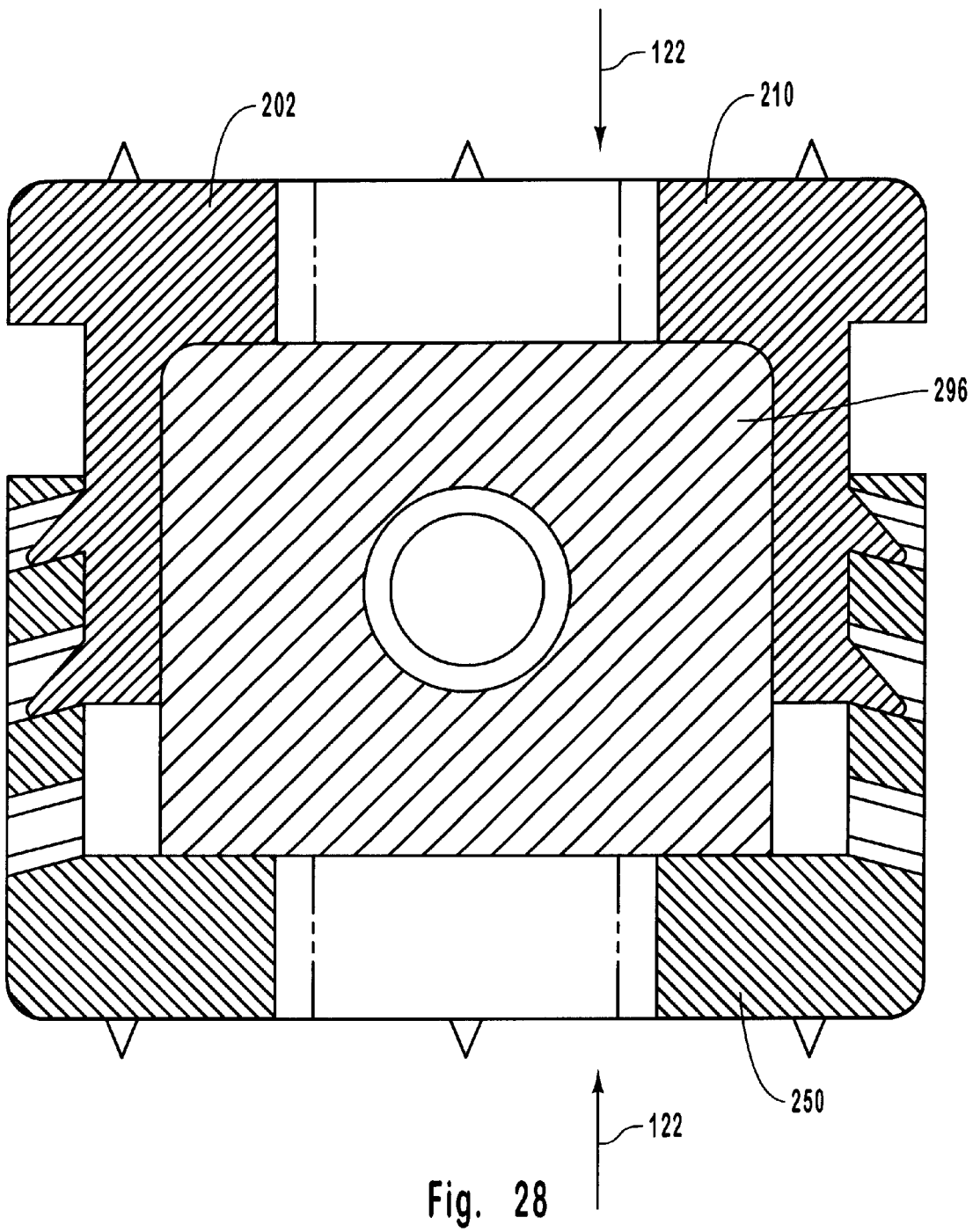
FIG. 28 is a cross sectional front view of a fusion implant showing an alternative embodiment of a reinforcing member.

In an alternative embodiment depicted in FIG. 28, a reinforcing member 296 is shown within housing 202. Reinforcing member 296 is the same as reinforcing member 204 except that support shelf 292 has been removed. In this embodiment, compressive force 122 is primarily carried by reinforcing member 296 as a result of reinforcing member 296 being compressed between the interior faces of cap plate 210 and base plate 250.

In one embodiment, each of the components of fusion implant 200 and the alternatives thereof can be made in the same way and from the same materials and alternatives thereof as previously discussed with regard to fusion implant 10. In an alternative embodiment, reinforcing members 204 and 296 can be comprised of an osteogenic substance and more commonly bone.

Fusion implant 200 is used in substantially the same way as previously discussed with regard to fusion implant 10 in FIGS. 7–15. Specifically, distal end 166 of inserter 162 is inserted into access mouth 274 of housing 202, passes through compartment 273, and screwed into aperture 238 on attachment wall 236. Either before or after the insertion of distraction tool 164 within compartment 273, housing 202 of fusion implant 200 is inserted between desired bone, such as between vertebrae. Although not required the insertion of housing 202 can be guided by the use of inserter 162.

Once housing 202 is appropriately positioned, distraction tool 164 is used to expand housing 202 to a desired size. After removal of distraction tool 164 from housing 202, a correspondingly sized reinforcing member 204 or 296 is passed over inserter 162 by sliding inserter 162 through passageway 302. Reinforcing member 204, 296 is advanced along inserter 162 until reinforcing member 204, 296 is received within compartment 273. Although not required, in one method the end of tubular push rod 182 is initially screwed into passageway 302 of reinforcing member 204, 296. Inserter 162 is then passed through both the reinforcing member and tubular push rod 182. Push rod 182 is used to control the advance of reinforcing member 204, 296 into compartment 273 and, if desired, facilitate removal of reinforcing member 204, 296 from compartment 273. Once reinforcing member 204 is appropriately positioned within compartment 273, both push rod 180 and inserter 162 are removed.

Figure 29:
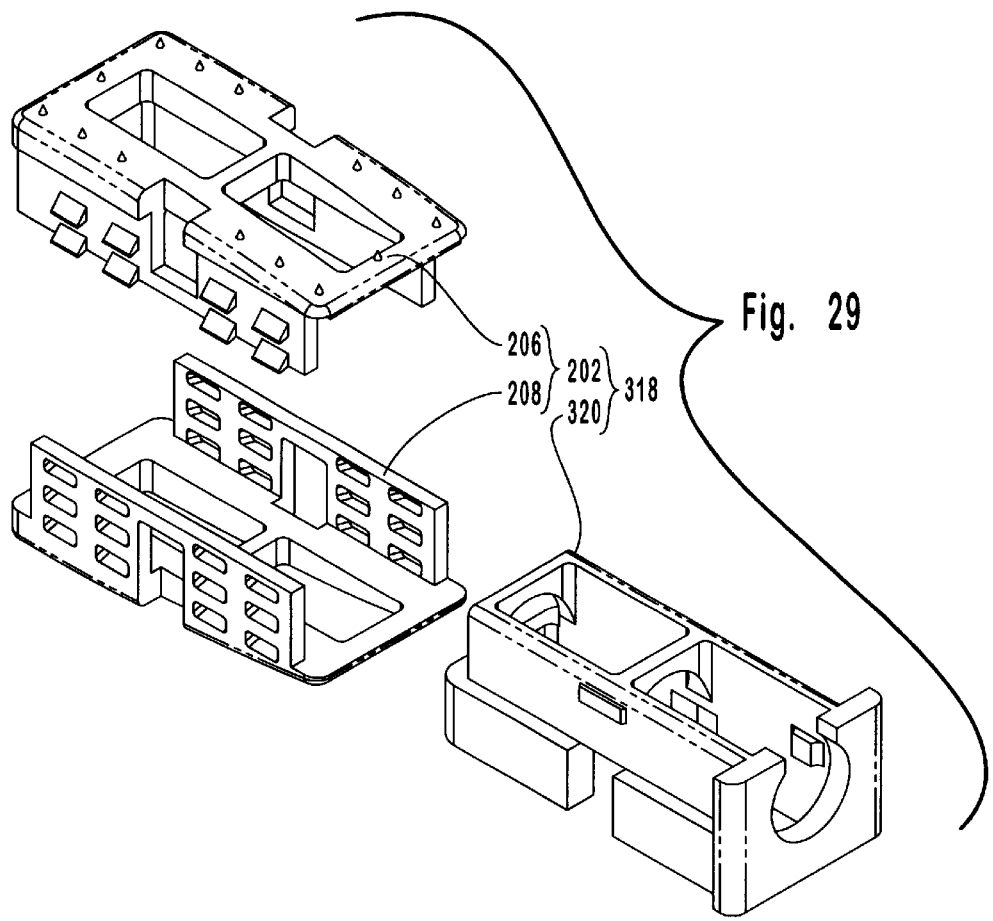
FIG. 29 is a perspective view of another alternative embodiment of a bone fusion implant in a disassembled state.
Figure 30:
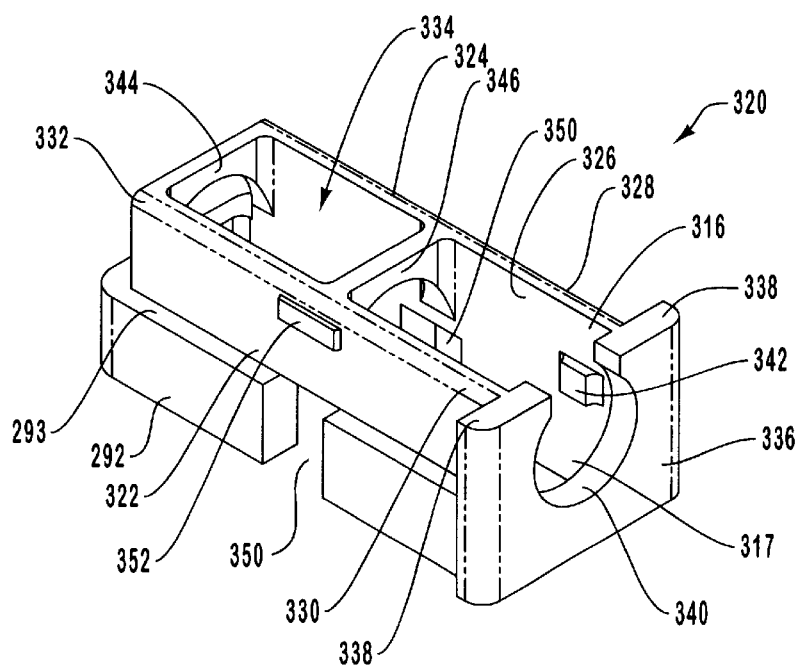
FIG. 30 is a front perspective view of a reinforcing member of the embodiment shown in FIG. 29.
Figure 31:
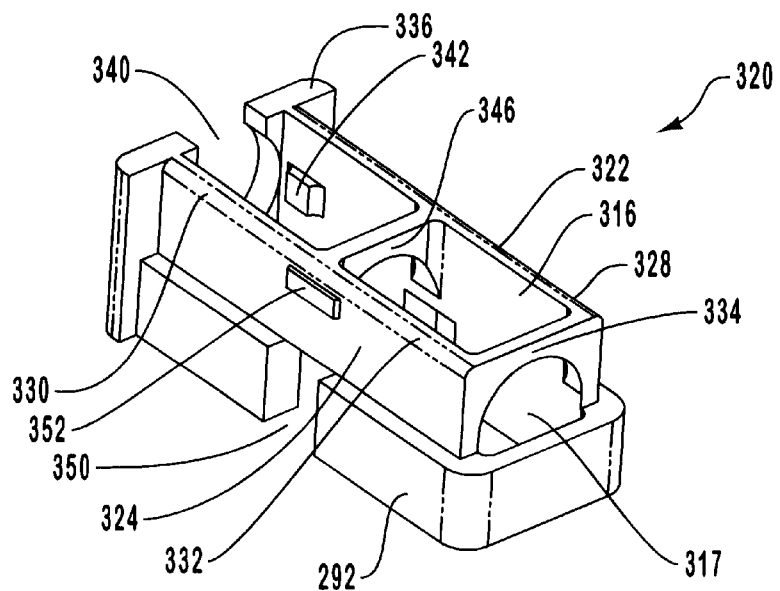
FIG. 31 is a back perspective view of the reinforcing member shown in FIG. 30.
Figure 32:
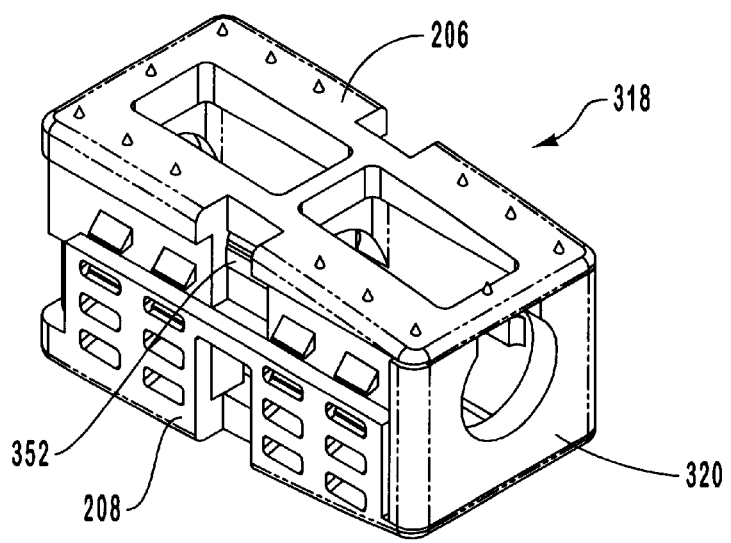
FIG. 32 is a perspective view of the bone fusion implant shown in FIG. 29 in an assembled state.

Depicted in FIG. 29 is yet another alternative embodiment of a bone fusion implant 318. Bone fusion implant 318 comprises housing 202 as previously discussed with regard to fusion implant 200. In contrast to fusion implant 200, however, fusion implant 318 comprises a reinforcing member 320. As depicted in FIGS. 30 and 31, reinforcing member 320 comprises a pair of upstanding spaced apart walls 322 and 324 disposed in substantially parallel alignment. Each wall 322 and 324 has an inside face 326 and an opposing outside face 328 extending between a proximal end 330 and an opposing distal end 332. Each wall 322 and 324 also has a top end 316 and an opposing bottom end 317. Bounded between walls 322 and 324 is an open channel 334.

Extending between walls 322 and 324 at proximal end 330 is a face plate 336. Face plate 336 includes a flange 338 that projects beyond outside face 328 of each wall 322 and 324. An opening 340 extends through face plate 336 so as to communicate with channel 334. Face plate 336 also has a top surface 342 through which opening 340 extends.

To further secure the placement of walls 322 and 324, a distal brace 344 extends between walls 322 and 324 at top end 316 of distal end 332. Similarly, a central brace 346 extends between walls 322 and 324 at top end 316 between proximal end 330 and distal end 332. Support shelf 292, as previously discussed with regard to reinforcing member 204, outwardly extends from the bottom end 317 of walls 322 and 324 and extends between walls 322 and 324 at distal end 332. A side port 350 extends through each wall 322 and 324 and overlapping support shelf 292 at a substantially central location between proximal end 330 and distal end 332. Furthermore, outwardly projecting from outside face 328 of each wall 322 and 324 above support shelf 292 is a detent 352.

In one embodiment of the present invention, means are provided for removably connecting an insertion tool to reinforcing member 320. By way of example and not by limitation, inwardly projecting from inside face 326 of each wall 322 and 324 adjacent to opening 340 is a bayonet prong 342. Each bayonet prong 342 projects into alignment with opening 340. Accordingly by forming a bayonet connector on the end of push rod 182, push rod 102 can be inserted into opening 340 and then rotated to engage bayonet prongs 342. In alternative embodiments, threads or other interlocking structures can be formed on face plate 336 or walls 322 and 324. The other alternatives as discussed with the other means for removably connecting can also be used.

As with the other previously discussed reinforcing members, reinforcing member 320 comes in a variety of different sizes. As depicted in FIG. 29, each different size of reinforcing member 320 is configured to fit within compartment 273 of housing 202 when housing 202 is expanded to the corresponding size.

When in the fully assembled configuration, walls 322 and 324 of reinforcing member 320 are compressed between the interior faces of cap plate 210 and base plate 250 when compressive force 122 is applied. Similarly, support shelf 292 of reinforcing member 320 is compressed between support members 226, 228 and base plate 250. As such, when reinforcing member 320 is inserted within compartment 273 and compressive force 122 is applied to fusion implant 318, compressive force 102 is primarily carried through reinforcing member 320 as opposed to between teeth 242 and adjustment holes 270.

During use, housing 202 is inserted and expanded between bone as previously discussed with regard to fusion implants 10 and 200. Next, the end of tubular push rod 182 is inserted through opening 340 of face plate 336 of reinforcing member 320 and rotated to establish the removable bayonet connection as previously discussed. Reinforcing member 320 is then passes over inserter 162 so that inserter 162 is received within channel 334 of reinforcing member 320 and within tubular push rod 182. Push rod 182 is then used to advance reinforcing member 320 into compartment 273 through access mouth 274. Once reinforcing member 320 is appropriately positioned within compartment 273, inserter 162 is removed. An osteogenic substance is then passed down through push rod 182 so as to pack channel 334 therewith. Once packed, push rod 182 is removed.

Figure 33:
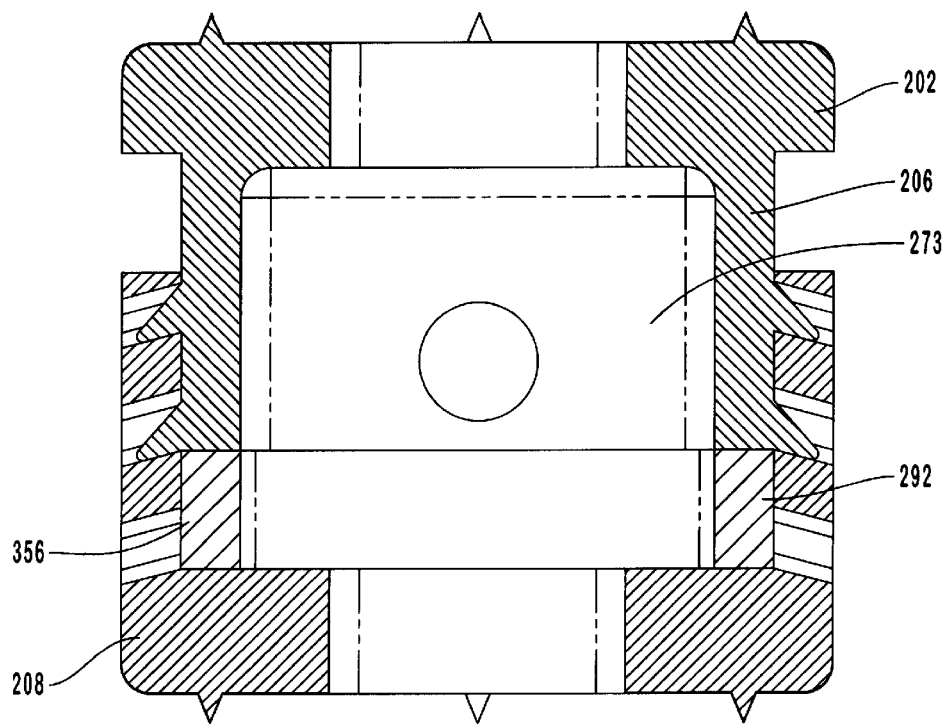
FIGS. 33–35 are cross sectional front views of alternative embodiments of reinforcing members positioned within the housing of the embodiment shown in FIG. 29.
Figure 34:
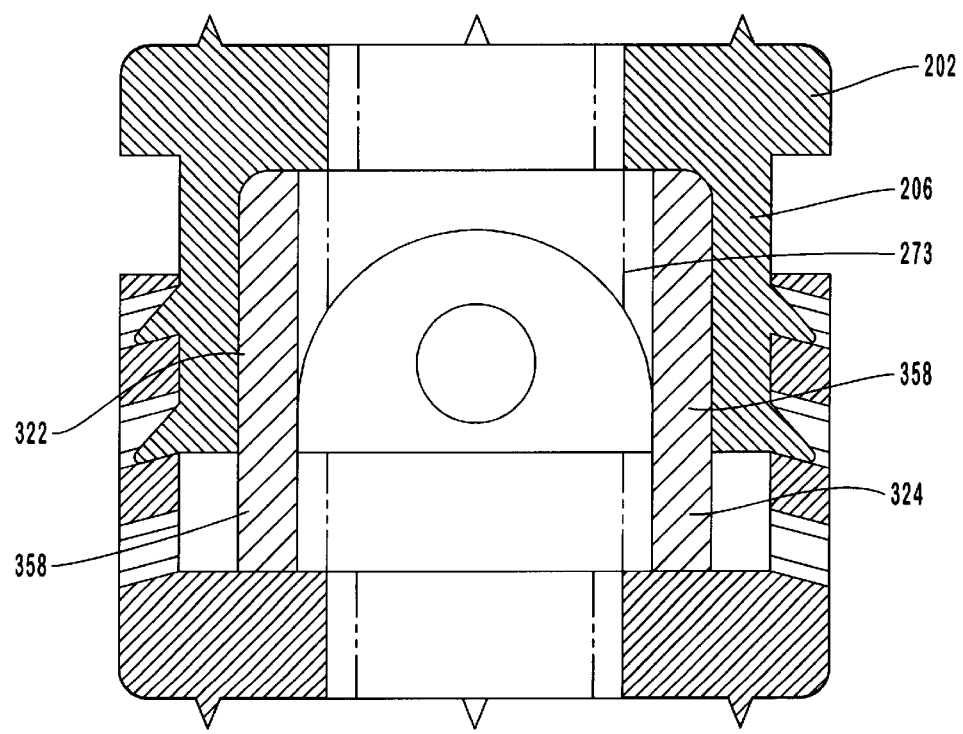
Figure 35:
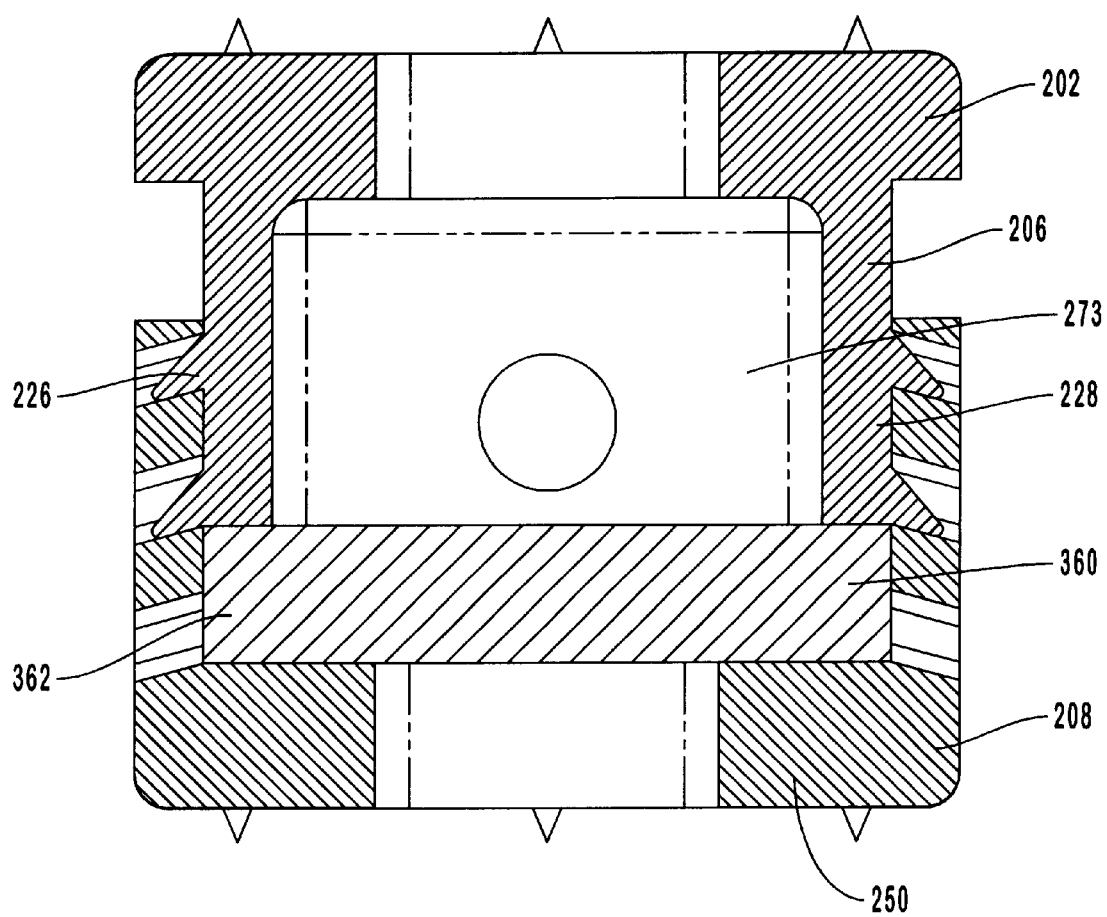

Depicted in FIGS. 33–35 are other alternative embodiments of reinforcing member. For example, depicted in FIG. 33 is a reinforcing member 356 shown disposed within compartment 273 of housing 202. Reinforcing member 356 comprises support shelf 292, as previously discussed with regard to reinforcing member 320. Attached to support shelf 292, but not shown, is face plate 198 as previously discussed with regard to reinforcing member 197.

Depicted in FIG. 34 is a reinforcing member 358. Reinforcing member 358 is substantially the same as reinforcing member 320 except that support shelf 292 has been removed.

Finally, depicted in FIG. 35 is a reinforcing member 360. Reinforcing member 360 comprises a plate 362 which is configured to rest on the inside face of base plate 250 so as to be compressed between support members 226, 228 and base plate 250 when compressive force 122 is applied. A face plate or other structure is formed at the front of plate 250 with means for removably connecting an insertion tool formed thereon. Reinforcing members 320, 356, 358, and 380 can be made in the same way and from the same materials as discussed with regard to the other reinforcing member.

The present invention may be embodied in other specific forms without departing from its spirit or essential characteristics. For example, as illustrated above with regard to reinforcing member 356, 358, and 380, elements of the various illustrated embodiments can be mixed and matched to form a variety of yet other embodiments. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An adjustable bone fusion implant comprising:
   a first plate having an interior face and an opposing exterior face;
   a second plate having an interior face and an opposing exterior face;
   means for connecting the first plate to the second plate such that the first plate and the second plate can be selectively manually separated to one or more predefined positions and such that the first plate and the second plate are mechanically stopped from collapsing toward each other once separated to the one or more predefined positions; and
   a discrete reinforcing member removably positioned between the first plate and the second plate.

2. An adjustable bone fusion implant as recited in claim 1, wherein the discrete reinforcing member is removably slid between the first plate and the second plate.

3. An adjustable bone fusion implant as recited in claim 1, wherein the reinforcing member is removably positioned between the first plate and the second plate such that the reinforcing member biases against the first plate and the second plate when a compressive force is applied on the first plate and the second plate.

4. An adjustable bone fusion implant as recited in claim 1, wherein the means for connecting comprises:
   a pair of spaced apart first support members projecting from the first plate, at least one of the first support members having a plurality of teeth projecting therefrom; and
   a pair of spaced apart second support members projecting from the second plate, at least one of the second support members having at least one hole formed thereon, at least one of the plurality of teeth of the first support member being disposed within the hole of the second support member.

5. An adjustable bone fusion implant as recited in claim 4, wherein the at least one tooth on the first support member comprises:
   a top surface intersecting with the first support member so as to form a first inside angle relative to the first support member that is less than 90°; and
   a bottom surface intersecting with the first support member so as to form a second inside angle relative to the first support member that is less than 90°, the top surface intersecting with the bottom surface at an outer edge.

6. An adjustable bone fusion implant as recited in claim 5, wherein the second inside angle is greater than the first inside angle.

7. An adjustable bone fusion implant as recited in claim 1, wherein the exterior face of the first plate is angled relative to the exterior face of the second plate so as to form a wedged shape configuration.

8. An adjustable bone fusion implant as recited in claim 1, further comprising:
   an attachment wall projecting from the first plate or the second plate toward the other of the first plate or the second plate; and
   means formed on the attachment wall for removably connecting an insertion tool to the attachment wall.

9. An adjustable bone fusion implant as recited in claim 8, wherein the means for removably connecting an insertion tool the attachment wall comprises a threaded opening extending at least partially through the attachment wall.

10. An adjustable bone fusion implant as recited in claim 1, further comprising at least one grafting port extending through at least the first plate or the second plate.

11. An adjustable bone fusion implant as recited in claim 1, wherein the reinforcing member comprises a block having a front face and an opposing back face with a passageway extending therebetween.

12. An adjustable bone fusion implant as recited in claim 1, wherein the reinforcing member comprises a block, the block being comprised of bone.

13. An adjustable bone fusion implant as recited in claim 1, wherein the reinforcing member comprises a pair of spaced apart walls with a substantially open channel longitudinally extending therebetween.

14. An adjustable bone fusion implant as recited in claim 1, wherein a compartment is at least partially bounded between the first plate and the second plate, the reinforcing member being at least partially disposed within the compartment.

15. An adjustable bone fusion implant as recited in claim 1, wherein the reinforcing member has a substantially U-shaped configuration.

16. An adjustable bone fusion implant comprising:
   a housing comprising a top surface, a bottom surface and a pair of spaced apart expandable sidewalls extending therebetween, the top surface, bottom surface, and pair of expandable sidewalls at least partially bounding a compartment therebetween the expandable sidewalls including at least one mechanical stop that prevents collapsing of the sidewalls once expanded; and
   a discrete reinforcing member of a predetermined shape positioned in the compartment such that a compressive force applied on the top surface and bottom surface of the housing is transferred through the reinforcing member.

17. An adjustable bone fusion implant as recited in claim 16, wherein the reinforcing member is removably positioned within the compartment of the housing.

18. An adjustable bone fusion implant as recited in claim 17, wherein the reinforcing member is removably slid within the compartment of the housing.

19. An adjustable bone fusion implant as recited in claim 16, wherein the reinforcing member comprises a block having a front face and an opposing back face with a passageway extending therebetween.

20. An adjustable bone fusion implant as recited in claim 16, wherein the reinforcing member comprises a block, the block being comprised of bone.

21. An adjustable bone fusion implant as recited in claim 16, wherein the reinforcing member comprises a pair of spaced apart walls with a substantially open channel longitudinally extending therebetween.

22. An adjustable bone fusion implant as recited in claim 16, wherein the reinforcing member is comprised of plastic or metal.

23. An adjustable bone fusion implant as recited in claim 16, wherein the expandable sidewalls comprise:
   a pair of spaced apart first support members each having a plurality of teeth projecting therefrom; and
   a pair of spaced apart second support members each having a plurality of holes formed thereon, at least one of the plurality of teeth of each of the first support members being disposed within one of the plurality of holes of a corresponding second support member.

24. An adjustable bone fusion implant as recited in claim 23, wherein the housing further comprises:

an attachment wall projecting into the compartment at least partially between the first support members; and means formed on the attachment wall for removably connecting an insertion tool to the attachment wall.

25. An adjustable bone fusion implant as recited in claim 16, wherein the top surface of the housing is angled relative to the bottom surface of the housing so that the housing has a substantially wedged shaped configuration.

26. An adjustable bone fusion implant as recited in claim 16, further comprising means formed on the reinforcing member for removably connecting an insertion tool to the reinforcing member.

27. An adjustable bone fusion implant comprising:

a first plate having an interior face and an opposing exterior face;

a pair of spaced apart first support members projecting from the first plate, at least one of the first support members having a plurality of teeth projecting therefrom;

a second plate having an interior face and an opposing exterior face, the interior face of the first plate facing the interior face of the second plate such that a compartment is at least partially bound therebetween;

a pair of spaced apart second support members projecting from the second plate, at least one of the second support members having at least one hole formed thereon, at least one of the plurality of teeth of the first support member being disposed within the hole of the second support member; and a discrete reinforcing member of a predetermined shape disposed between the first plate and the second plate.

28. An adjustable bone fusion implant as recited in claim 27, wherein the discrete reinforcing member is disposed within the compartment.

29. An adjustable bone fusion implant as recited in claim 27, wherein the discrete reinforcing member is removably disposed between the first plate and the second plate.

30. An adjustable bone fusion implant as recited in claim 27, wherein the exterior face of the first plate is angled relative to the exterior face of the second plate so as to form a wedged shape configuration.

31. An adjustable bone fusion implant as recited in claim 27, wherein at least one of the plurality of teeth of the first support member comprises a sloping surface and an intersecting horizontally disposed surface.

32. An adjustable bone fusion implant as recited in claim 27, further comprising at least one grafting port extending through at least the first plate or the second plate to the compartment.

33. An adjustable bone fusion implant as recited in claim 27, further comprising a plurality of retention barbs projecting from the exterior face of at least the first plate or the second plate.

34. An adjustable bone fusion implant kit comprising:

a housing comprising a top surface, a bottom surface, and a pair of spaced apart expandable sidewalls extending therebetween, the top surface and the bottom surface at least partially bounding a compartment therebetween, the expandable sidewalls being selectively expandable so that the compartment is correspondingly expandable between a plurality of predefined sizes, the expandable sidewalls including at least one mechanical stop that prevents collapsing of the sidewalls once expanded; and a plurality of discrete reinforcing members, each reinforcing member having a different size corresponding to one of the plurality of predefined sizes of the compartment, each of the reinforcing members being configured to be inserted into the compartment when the compartment is adjusted to the size of the corresponding reinforcing insert.

35. An adjustable bone fusion implant kit as recited in claim 34, wherein the expandable sidewalls are configured to expand in predefined increments.

36. An adjustable bone fusion implant kit as recited in claim 34, wherein at least one of the reinforcing members comprises a block having a front face and an opposing back face with a passageway extending therebetween.

37. An adjustable bone fusion implant kit as recited in claim 34, wherein at least one of the reinforcing members comprises a pair of spaced apart walls with a substantially open channel longitudinally extending therebetween.

* * * * *

UNITED STATES PATENT AND TRADEMARK OFFICE
CERTIFICATE OF CORRECTION

PATENT NO. : 6,562,074 B2
DATED : May 13, 2003
INVENTOR(S) : Daniel E. Gerbec et al.

It is certified that error appears in the above-identified patent and that said Letters Patent is hereby corrected as shown below:

<u>Title page,</u>
Item [75], Inventors, after "Wade Fallin," change "Hyde Part," to -- Hyde Park, --

<u>Column 6,</u>
Line 32, before "bottom" change "slopping" to -- sloping --

<u>Column 10,</u>
Line 46, before "housing" change "with" to -- within --

<u>Column 12,</u>
Line 17, before "outside" change "form" to -- from --
Line 44, after "outwardly" change "projecting" to -- project --
Line 46, before "base" insert -- to --

<u>Column 16,</u>
Line 30, before "over" change "passes" to -- passed --

Signed and Sealed this

Ninth Day of September, 2003

JAMES E. ROGAN
*Director of the United States Patent and Trademark Office*